(12) United States Patent
Palmer et al.

(10) Patent No.: US 8,142,442 B2
(45) Date of Patent: *Mar. 27, 2012

(54) SNARE

(75) Inventors: Olin Palmer, Mountain View, CA (US); Christopher T. Shen, Stanford, CA (US); Robert LaDuca, Davenport, CA (US); Larry Voss, San Jose, CA (US); Saypin Phonthalasa, San Frandisco, CA (US)

(73) Assignee: Abbott Laboratories, Abbott Park, IL (US)

( * ) Notice: Subject to any disclaimer, the term of this patent is extended or adjusted under 35 U.S.C. 154(b) by 1002 days.

This patent is subject to a terminal disclaimer.

(21) Appl. No.: 12/111,870

(22) Filed: Apr. 29, 2008

(65) Prior Publication Data

US 2008/0275497 A1    Nov. 6, 2008

Related U.S. Application Data

(60) Continuation of application No. 11/125,578, filed on May 10, 2005, now abandoned, which is a continuation of application No. 10/457,491, filed on Jun. 9, 2003, now Pat. No. 6,913,612, which is a division of application No. 10/123,896, filed on Apr. 15, 2002, now Pat. No. 6,592,607, which is a continuation of application No. 09/469,431, filed on Dec. 23, 1999, now Pat. No. 6,402,771.

(51) Int. Cl.
   *A61B 17/24*    (2006.01)
(52) U.S. Cl. ..................................... 606/113
(58) Field of Classification Search ............. 606/1, 113, 606/114, 127, 159, 200; 600/434, 585
   See application file for complete search history.

(56) References Cited

U.S. PATENT DOCUMENTS

| | | | |
|---|---|---|---|
| 2,943,626 A | 7/1960 | Dormia |
| 3,952,747 A | 4/1976 | Kimmell, Jr. |
| 4,347,846 A | 9/1982 | Dormia |
| 4,425,908 A | 1/1984 | Simon |
| 4,494,531 A | 1/1985 | Gianturco |
| 4,611,594 A | 9/1986 | Grayhack et al. |
| 4,612,931 A | 9/1986 | Dormia |
| 4,619,246 A | 10/1986 | Molgaard-Nielsen et al. |
| 4,643,184 A | 2/1987 | Mobin-Uddin |
| 4,650,466 A | 3/1987 | Luther |

(Continued)

FOREIGN PATENT DOCUMENTS

EP    0427429 A3    9/1991

(Continued)

OTHER PUBLICATIONS

Dilitation of the Carotid Artery By A Temporary Carotid Filter By A. Beck, St. Milic, A.M. Spagnoli, Nov.-Dec. Issue of OPLITAI, An International Journal on Military Medicine and Health Emergencies, pp. 67-74. Minibasket for Percutaneous Embolectomy and Filter ProtectionAgainst Distal Embolization: Technical Note.

*Primary Examiner* — Kevin T Truong
(74) *Attorney, Agent, or Firm* — Fulwider Patton LLP; Jonathan Feuchtwang

(57) ABSTRACT

An intravascular snare device for use in capturing debris found in blood vessels. The snare device is fabricated from a tube and includes longitudinally and circumferentially extending members. The snare device specifically embodies structure that provides enhanced radial opening and angular resistance to collapse.

16 Claims, 9 Drawing Sheets

U.S. PATENT DOCUMENTS

| | | |
|---|---|---|
| 4,662,885 A | 5/1987 | DiPisa, Jr. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,865,017 A | 9/1989 | Shinozuka |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |
| 5,092,839 A | 3/1992 | Kipperman |
| 5,100,423 A | 3/1992 | Fearnot |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,154,705 A * | 10/1992 | Fleischhacker et al. ...... 600/585 |
| 5,158,548 A | 10/1992 | Lau |
| 5,160,342 A | 11/1992 | Reger et al. |
| 5,171,233 A | 12/1992 | Amplatz et al. |
| 5,192,286 A | 3/1993 | Phan et al. |
| 5,234,458 A | 8/1993 | Metais |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,375,612 A | 12/1994 | Cottenceau et al. |
| 5,383,887 A | 1/1995 | Nadal |
| 5,421,832 A | 6/1995 | Lefebvre |
| 5,486,183 A | 1/1996 | Middleman et al. |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,509,923 A | 4/1996 | Middleman et al. |
| 5,549,626 A | 8/1996 | Miller et al. |
| 5,601,572 A | 2/1997 | Middleman et al. |
| 5,601,595 A | 2/1997 | Smith |
| 5,613,981 A | 3/1997 | Boyle et al. |
| 5,626,605 A | 5/1997 | Irie et al. |
| 5,634,942 A | 6/1997 | Chevillon et al. |
| 5,649,953 A | 7/1997 | Lefebvre |
| 5,658,296 A | 8/1997 | Bates et al. |
| 5,662,671 A | 9/1997 | Barbut et al. |
| 5,662,703 A | 9/1997 | Yurek et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,706,826 A * | 1/1998 | Schwager ...... 600/585 |
| 5,709,704 A | 1/1998 | Nott et al. |
| 5,720,754 A | 2/1998 | Middleman et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A | 6/1998 | Nakhjavan |
| 5,776,162 A | 7/1998 | Kleshinski |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,820,628 A | 10/1998 | Middleman et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maas |
| 5,848,964 A | 12/1998 | Samuels |
| 5,868,708 A | 2/1999 | Hart et al. |
| 5,876,367 A | 3/1999 | Kaganov et al. |
| 5,895,398 A | 4/1999 | Wensel et al. |
| 5,897,567 A | 4/1999 | Ressemann et al. |
| 5,902,263 A | 5/1999 | Patterson et al. |
| 5,904,690 A | 5/1999 | Middleman et al. |
| 5,910,154 A | 6/1999 | Tsugita et al. |
| 5,911,734 A | 6/1999 | Tsugita et al. |
| 5,935,139 A | 8/1999 | Bates |
| 5,941,869 A | 8/1999 | Patterson et al. |
| 5,941,896 A | 8/1999 | Kerr |
| 5,944,728 A | 8/1999 | Bates |
| 5,954,745 A | 9/1999 | Gertler et al. |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,007,557 A | 12/1999 | Ambrisco et al. |
| 6,013,093 A | 1/2000 | Nott et al. |
| 6,022,336 A | 2/2000 | Zadno-Azizi et al. |
| 6,027,520 A | 2/2000 | Tsugita et al. |
| 6,042,598 A | 3/2000 | Tsugita et al. |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,074,357 A | 6/2000 | Kaganov et al. |
| 6,086,605 A | 7/2000 | Barbut et al. |
| 6,090,097 A | 7/2000 | Barbut et al. |
| 6,096,053 A | 8/2000 | Bates |
| 6,099,534 A | 8/2000 | Bates et al. |
| 6,099,549 A | 8/2000 | Bosma et al. |
| 6,117,154 A | 9/2000 | Barbut et al. |
| 6,129,739 A | 10/2000 | Khosravi |
| 6,136,015 A | 10/2000 | Kurz |
| 6,136,016 A | 10/2000 | Barbut et al. |
| 6,142,987 A | 11/2000 | Tsugita |
| 6,152,946 A | 11/2000 | Broome et al. |
| 6,152,947 A | 11/2000 | Ambrisco et al. |
| 6,165,198 A | 12/2000 | McGurk et al. |
| 6,165,200 A | 12/2000 | Tsugita et al. |
| 6,168,579 B1 | 1/2001 | Tsugita et al. |
| 6,168,603 B1 | 1/2001 | Leslie et al. |
| 6,168,604 B1 | 1/2001 | Cano |
| 6,171,327 B1 | 1/2001 | Daniel et al. |
| 6,171,328 B1 | 1/2001 | Addis |
| 6,174,318 B1 | 1/2001 | Bates et al. |
| 6,176,849 B1 | 1/2001 | Yang et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,203,561 B1 | 3/2001 | Ramee et al. |
| 6,206,868 B1 | 3/2001 | Parodi |
| 6,214,026 B1 | 4/2001 | Lepak et al. |
| 6,214,040 B1 | 4/2001 | Jayaraman |
| 6,224,620 B1 | 5/2001 | Maahs |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 | 6/2001 | Addis |
| 6,245,088 B1 | 6/2001 | Lowery |
| 6,245,089 B1 | 6/2001 | Daniel et al. |
| 6,251,119 B1 | 6/2001 | Addis |
| 6,251,122 B1 | 6/2001 | Tsukernik |
| 6,254,633 B1 | 7/2001 | Pinchuk et al. |

| | | | | | | |
|---|---|---|---|---|---|---|
| 6,258,115 | B1 | 7/2001 | Dubrul | 6,520,978 | B1 | 2/2003 | Blackledge et al. |
| 6,258,120 | B1 | 7/2001 | McKenzie et al. | 6,527,746 | B1 | 3/2003 | Oslund et al. |
| 6,264,663 | B1 | 7/2001 | Cano | 6,527,791 | B2 | 3/2003 | Fisher |
| 6,264,672 | B1 | 7/2001 | Fisher | 6,530,939 | B1 | 3/2003 | Hopkins et al. |
| 6,267,776 | B1 | 7/2001 | O'Connell | 6,530,940 | B2 | 3/2003 | Fisher |
| 6,267,777 | B1 | 7/2001 | Bosma et al. | 6,533,800 | B1 | 3/2003 | Barbut |
| 6,270,477 | B1 | 8/2001 | Bagaosian | 6,537,294 | B1 | 3/2003 | Boyle et al. |
| 6,270,513 | B1 | 8/2001 | Tsugita et al. | 6,537,295 | B2 | 3/2003 | Petersen |
| 6,273,901 | B1 | 8/2001 | Whitcher et al. | 6,537,296 | B2 | 3/2003 | Levinson et al. |
| 6,277,138 | B1 | 8/2001 | Levinson et al. | 6,537,297 | B2 | 3/2003 | Tsugita et al. |
| 6,277,139 | B1 | 8/2001 | Levinson et al. | 6,540,722 | B1 | 4/2003 | Boyle et al. |
| 6,280,451 | B1 | 8/2001 | Bates et al. | 6,540,767 | B1 | 4/2003 | Walak et al. |
| 6,287,321 | B1 | 9/2001 | Jang | 6,540,768 | B1 | 4/2003 | Diaz et al. |
| 6,290,656 | B1 | 9/2001 | Boyle et al. | 6,544,276 | B1 | 4/2003 | Azizi |
| 6,290,710 | B1 | 9/2001 | Cryer et al. | 6,544,279 | B1 | 4/2003 | Hopkins et al. |
| 6,295,989 | B1 | 10/2001 | Connors, III | 6,544,280 | B1 | 4/2003 | Daniel et al. |
| 6,306,163 | B1 | 10/2001 | Fitz | 6,547,759 | B1 | 4/2003 | Fisher |
| 6,319,242 | B1 | 11/2001 | Patterson et al. | 6,551,268 | B1 | 4/2003 | Kaganov et al. |
| 6,319,268 | B1 | 11/2001 | Ambrisco et al. | 6,551,341 | B2 | 4/2003 | Boylan et al. |
| 6,325,815 | B1 | 12/2001 | Kusleika et al. | 6,551,342 | B1 | 4/2003 | Shen et al. |
| 6,336,934 | B1 | 1/2002 | Gilson et al. | 6,558,401 | B1 | 5/2003 | Azizi |
| 6,340,364 | B2 | 1/2002 | Kanesaka | 6,558,405 | B1 | 5/2003 | McInnes |
| 6,340,465 | B1 | 1/2002 | Hsu et al. | 6,562,058 | B2 | 5/2003 | Seguin |
| 6,346,116 | B1 | 2/2002 | Brooks et al. | 6,565,591 | B2 | 5/2003 | Kelly et al. |
| 6,348,056 | B1 | 2/2002 | Bates et al. | 6,569,184 | B2 | 5/2003 | Huter |
| 6,355,051 | B1 | 3/2002 | Sisskind et al. | 6,575,995 | B1 | 6/2003 | Huter et al. |
| 6,361,545 | B1 | 3/2002 | Macoviak et al. | 6,575,996 | B1 | 6/2003 | Denison et al. |
| 6,361,546 | B1 | 3/2002 | Khosravi | 6,575,997 | B1 | 6/2003 | Palmer et al. |
| 6,364,895 | B1 | 4/2002 | Greenhalgh | 6,582,447 | B1 | 6/2003 | Patel et al. |
| 6,364,896 | B1 | 4/2002 | Addis | 6,582,448 | B1 | 6/2003 | Boyle et al. |
| 6,364,900 | B1 | 4/2002 | Heuser | 6,585,756 | B1 | 7/2003 | Strecker |
| 6,371,969 | B1 | 4/2002 | Tsugita et al. | 6,589,263 | B1 | 7/2003 | Hopkins et al. |
| 6,371,970 | B1 | 4/2002 | Khosravi et al. | 6,589,265 | B1 | 7/2003 | Palmer et al. |
| 6,371,971 | B1 | 4/2002 | Tsugita et al. | 6,592,546 | B1 | 7/2003 | Barbut et al. |
| 6,375,670 | B1 | 4/2002 | Greenhalgh | 6,592,606 | B2 | 7/2003 | Huter et al. |
| 6,383,205 | B1 * | 5/2002 | Samson et al. ............... 606/200 | 6,592,607 | B1 | 7/2003 | Palmer et al. |
| 6,383,206 | B1 | 5/2002 | Gillick et al. | 6,592,616 | B1 | 7/2003 | Stack et al. |
| 6,384,062 | B1 | 5/2002 | Ikeda et al. | 6,596,011 | B2 | 7/2003 | Johnson et al. |
| 6,391,044 | B1 | 5/2002 | Yadav et al. | 6,599,307 | B1 | 7/2003 | Huter et al. |
| 6,394,978 | B1 | 5/2002 | Boyle et al. | 6,599,308 | B2 | 7/2003 | Amplatz |
| 6,395,014 | B1 | 5/2002 | Macoviak et al. | 6,602,269 | B2 | 8/2003 | Wallace et al. |
| 6,398,756 | B2 | 6/2002 | Peterson et al. | 6,602,271 | B2 | 8/2003 | Adams et al. |
| 6,402,771 | B1 | 6/2002 | Palmer et al. | 6,602,272 | B2 | 8/2003 | Boylan et al. |
| 6,406,471 | B1 | 6/2002 | Jang et al. | 6,602,273 | B2 | 8/2003 | Marshall |
| 6,423,032 | B2 | 7/2002 | Parodi | 6,605,102 | B1 | 8/2003 | Mazzocchi et al. |
| 6,423,086 | B1 | 7/2002 | Barbut et al. | 6,605,111 | B2 | 8/2003 | Bose et al. |
| 6,425,909 | B1 | 7/2002 | Dieck et al. | 6,607,506 | B2 | 8/2003 | Kletschka |
| 6,428,559 | B1 | 8/2002 | Johnson | 6,610,077 | B1 | 8/2003 | Hancock et al. |
| 6,432,122 | B1 | 8/2002 | Gilson et al. | 6,616,679 | B1 | 9/2003 | Khosravi et al. |
| 6,436,121 | B1 | 8/2002 | Blom | 6,616,680 | B1 | 9/2003 | Thielen |
| 6,443,926 | B1 | 9/2002 | Kletschka | 6,616,681 | B2 | 9/2003 | Hanson et al. |
| 6,443,971 | B1 | 9/2002 | Boylan et al. | 6,616,682 | B2 | 9/2003 | Joergensen et al. |
| 6,443,972 | B1 | 9/2002 | Bosma | 6,620,148 | B1 | 9/2003 | Tsugita et al. |
| 6,443,979 | B1 | 9/2002 | Stalker et al. | 6,620,182 | B1 | 9/2003 | Khosravi |
| 6,447,530 | B1 | 9/2002 | Ostrovsky et al. | 6,623,450 | B1 | 9/2003 | Dutta |
| 6,447,531 | B1 | 9/2002 | Amplatz | 6,629,953 | B1 | 10/2003 | Boyd |
| 6,450,989 | B2 | 9/2002 | Dubrul et al. | 6,632,236 | B2 | 10/2003 | Hogendijk |
| 6,458,139 | B1 | 10/2002 | Palmer et al. | 6,632,241 | B1 | 10/2003 | Hancock et al. |
| 6,461,370 | B1 | 10/2002 | Gray et al. | 6,635,068 | B1 | 10/2003 | Dubrul et al. |
| 6,468,291 | B2 | 10/2002 | Bates et al. | 6,635,070 | B2 | 10/2003 | Leeflang et al. |
| 6,482,222 | B1 | 11/2002 | Bruckheimer et al. | 6,638,293 | B1 | 10/2003 | Makowner et al. |
| 6,485,456 | B1 | 11/2002 | Kletschka | 6,638,294 | B1 | 10/2003 | Palmer |
| 6,485,497 | B2 | 11/2002 | Wensel et al. | 6,645,220 | B1 | 11/2003 | Huter et al. |
| 6,485,500 | B1 | 11/2002 | Kokish et al. | 6,645,221 | B1 | 11/2003 | Richter |
| 6,485,501 | B1 | 11/2002 | Green | 6,645,223 | B2 | 11/2003 | Boyle et al. |
| 6,485,502 | B2 | 11/2002 | Don Michael et al. | 6,645,224 | B2 | 11/2003 | Gilson et al. |
| 6,485,507 | B1 | 11/2002 | Walak et al. | 6,652,480 | B1 | 11/2003 | Imran et al. |
| 6,494,895 | B2 | 12/2002 | Addis | 6,652,505 | B1 | 11/2003 | Tsugita et al. |
| 6,499,487 | B1 | 12/2002 | McKenzie et al. | 6,652,554 | B1 | 11/2003 | Wholey et al. |
| 6,500,166 | B1 | 12/2002 | Zadno Azizi et al. | 6,652,557 | B1 | 11/2003 | MacDonald |
| 6,506,203 | B1 | 1/2003 | Boyle et al. | 6,656,202 | B2 | 12/2003 | Papp et al. |
| 6,506,205 | B2 | 1/2003 | Goldberg et al. | 6,656,203 | B2 | 12/2003 | Roth et al. |
| 6,511,492 | B1 | 1/2003 | Rosenbluth | 6,656,204 | B2 | 12/2003 | Ambrisco et al. |
| 6,511,496 | B1 | 1/2003 | Huter et al. | 6,656,351 | B2 | 12/2003 | Boyle |
| 6,511,497 | B1 | 1/2003 | Braun et al. | 6,660,021 | B1 | 12/2003 | Palmer et al. |
| 6,511,503 | B1 | 1/2003 | Burkett et al. | 6,663,650 | B2 | 12/2003 | Sepetka et al. |
| 6,514,273 | B1 | 2/2003 | Voss et al. | 6,663,651 | B2 | 12/2003 | Krolik et al. |
| 6,517,550 | B1 | 2/2003 | Konya et al. | 6,663,652 | B2 | 12/2003 | Daniel et al. |
| 6,517,559 | B1 | 2/2003 | O'Connell | 6,673,090 | B2 | 1/2004 | Root et al. |

| Patent No. | Date | Inventor |
|---|---|---|
| 6,676,666 B2 | 1/2004 | Vrba et al. |
| 6,676,682 B1 | 1/2004 | Tsugita et al. |
| 6,676,683 B1 | 1/2004 | Addis |
| 6,679,902 B1 | 1/2004 | Boyle et al. |
| 6,679,903 B2 | 1/2004 | Kurz |
| 6,682,546 B2 | 1/2004 | Amplatz |
| 6,685,722 B1 | 2/2004 | Rosenbluth et al. |
| 6,689,151 B2 | 2/2004 | Becker et al. |
| 6,692,513 B2 | 2/2004 | Streeter et al. |
| 6,695,813 B1 | 2/2004 | Boyle et al. |
| 6,695,858 B1 | 2/2004 | Dubrul et al. |
| 6,695,864 B2 | 2/2004 | Macoviak et al. |
| 6,696,666 B2 | 2/2004 | Merdan et al. |
| 6,699,260 B2 | 3/2004 | Dubrul et al. |
| 6,702,834 B1 | 3/2004 | Boyle et al. |
| 6,706,055 B2 | 3/2004 | Douk et al. |
| 6,712,834 B2 | 3/2004 | Yassour et al. |
| 6,712,835 B2 | 3/2004 | Mazzocchi et al. |
| 6,716,231 B1 | 4/2004 | Rafiee et al. |
| 6,723,085 B2 | 4/2004 | Jang et al. |
| 6,726,701 B2 | 4/2004 | Gilson |
| 6,726,702 B2 | 4/2004 | Khosravi |
| 6,726,703 B2 | 4/2004 | Broome et al. |
| 6,740,061 B1 | 5/2004 | Oslund et al. |
| 6,743,247 B1 | 6/2004 | Levinson et al. |
| 6,746,469 B2 | 6/2004 | Mouw |
| 6,752,819 B1 | 6/2004 | Brady et al. |
| 6,755,846 B1 | 6/2004 | Yadav |
| 6,758,855 B2 | 7/2004 | Fulton, III et al. |
| 6,761,727 B1 | 7/2004 | Ladd |
| 6,773,448 B2 | 8/2004 | Kusleika et al. |
| 6,790,219 B1 | 9/2004 | Murphy |
| 6,793,666 B2 | 9/2004 | Hansen et al. |
| 6,793,668 B1 | 9/2004 | Fisher |
| 6,800,080 B1 | 10/2004 | Bates |
| 6,814,739 B2 | 11/2004 | Secrest et al. |
| 6,818,006 B2 | 11/2004 | Douk et al. |
| 6,837,898 B2 | 1/2005 | Boyle |
| 6,840,950 B2 | 1/2005 | Stanford et al. |
| 6,843,798 B2 | 1/2005 | Kusleika et al. |
| 6,846,316 B2 | 1/2005 | Abrams |
| 6,846,317 B1 | 1/2005 | Nigon |
| 6,863,696 B2 | 3/2005 | Kantsevitcha et al. |
| 6,866,677 B2 | 3/2005 | Douk et al. |
| 6,872,216 B2 | 3/2005 | Daniel et al. |
| 6,878,151 B2 | 4/2005 | Carrison et al. |
| 6,878,153 B2 | 4/2005 | Linder et al. |
| 6,887,256 B2 | 5/2005 | Gilson et al. |
| 6,887,257 B2 | 5/2005 | Salaheih et al. |
| 6,887,258 B2 | 5/2005 | Denison |
| 6,888,098 B1 | 5/2005 | Merdan et al. |
| 6,890,340 B2 | 5/2005 | Duane |
| 6,890,341 B2 | 5/2005 | Dieck et al. |
| 6,893,450 B2 | 5/2005 | Foster |
| 6,893,451 B2 | 5/2005 | Cano et al. |
| 6,896,690 B1 | 5/2005 | Lambrecht et al. |
| 6,896,691 B2 | 5/2005 | Boylan |
| 6,902,540 B2 | 6/2005 | Dorros et al. |
| 6,908,474 B2 | 6/2005 | Hogendijk et al. |
| 6,911,036 B2 | 6/2005 | Douk et al. |
| 6,913,612 B2 | 7/2005 | Palmer et al. |
| 6,918,921 B2 | 7/2005 | Brady et al. |
| 6,929,652 B1 | 8/2005 | Andrews |
| 6,932,830 B2 | 8/2005 | Ungs |
| 6,932,831 B2 | 8/2005 | Forber |
| 6,936,058 B2 | 8/2005 | Forde et al. |
| 6,936,059 B2 | 8/2005 | Belef |
| 6,939,361 B1 | 9/2005 | Kleshinski |
| 6,939,362 B2 | 9/2005 | Boyle et al. |
| 6,942,673 B2 | 9/2005 | Bates et al. |
| 6,949,103 B2 | 9/2005 | Mazzocchi et al. |
| 6,951,570 B2 | 10/2005 | Linder et al. |
| 6,953,471 B1 | 10/2005 | Lilly et al. |
| 6,953,472 B2 | 10/2005 | Palmer et al. |
| 6,958,074 B2 | 10/2005 | Russell |
| 6,960,370 B2 | 11/2005 | Monni et al. |
| 6,962,598 B2 | 11/2005 | Linder et al. |
| 6,964,670 B1 | 11/2005 | Shah |
| 6,964,672 B2 | 11/2005 | Brady |
| 6,964,673 B2 | 11/2005 | Tsugita et al. |
| 6,969,395 B2 | 11/2005 | Eskuri |
| 6,969,396 B2 | 11/2005 | Krolik et al. |
| 6,969,402 B2 | 11/2005 | Bales et al. |
| 6,970,730 B2 | 11/2005 | Fuimaono et al. |
| 6,972,025 B2 | 12/2005 | WasDyke |
| 6,973,340 B2 | 12/2005 | Fuimaono et al. |
| 6,974,468 B2 | 12/2005 | DoBrava et al. |
| 6,974,469 B2 | 12/2005 | Broome et al. |
| 6,979,343 B2 | 12/2005 | Russo |
| 6,979,344 B2 | 12/2005 | Jones et al. |
| 6,986,778 B2 | 1/2006 | Zadno-Azizi |
| 6,989,019 B2 | 1/2006 | Mazzocchi et al. |
| 6,989,021 B2 | 1/2006 | Bosma et al. |
| 6,989,027 B2 | 1/2006 | Allen et al. |
| 6,991,641 B2 | 1/2006 | Diaz et al. |
| 6,991,642 B2 | 1/2006 | Petersen |
| RE38,972 E | 2/2006 | Purdy |
| 6,994,718 B2 | 2/2006 | Groothuis et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,001,407 B2 | 2/2006 | Hansen et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,004,964 B2 | 2/2006 | Thompson et al. |
| 7,011,671 B2 | 3/2006 | Welch |
| 7,011,672 B2 | 3/2006 | Barbut et al. |
| 7,014,647 B2 | 3/2006 | Brady et al. |
| 7,018,372 B2 | 3/2006 | Casey |
| 7,018,385 B2 | 3/2006 | Bates et al. |
| 7,018,393 B1 | 3/2006 | Boyle et al. |
| 7,029,440 B2 | 4/2006 | Broome et al. |
| 7,033,375 B2 | 4/2006 | Mazocchi et al. |
| 7,037,320 B2 | 5/2006 | Brady et al. |
| 7,041,116 B2 | 5/2006 | Goto et al. |
| 7,044,958 B2 | 5/2006 | Douk et al. |
| 7,048,752 B2 | 5/2006 | Mazzocchi |
| 7,048,758 B2 | 5/2006 | Boyle et al. |
| 7,056,328 B2 | 6/2006 | Arnott |
| 7,060,082 B2 | 6/2006 | Goll et al. |
| 7,077,854 B2 | 7/2006 | Khosravi |
| 7,094,243 B2 | 8/2006 | Mulholland |
| 7,094,249 B1 | 8/2006 | Broome et al. |
| 7,097,440 B2 | 8/2006 | Papp et al. |
| 7,097,651 B2 | 8/2006 | Harrison et al. |
| 7,101,380 B2 | 9/2006 | Khachin et al. |
| 7,108,707 B2 | 9/2006 | Huter et al. |
| 2002/0091408 A1 | 7/2002 | Sutton et al. |
| 2002/0091409 A1 | 7/2002 | Sutton et al. |
| 2002/0095141 A1 | 7/2002 | Belef et al. |
| 2002/0099407 A1 | 7/2002 | Becker et al. |
| 2002/0103501 A1 | 8/2002 | Diaz et al. |
| 2002/0107541 A1 | 8/2002 | Vale et al. |
| 2002/0111648 A1 | 8/2002 | Kusleika et al. |
| 2002/0111649 A1 | 8/2002 | Russo et al. |
| 2002/0115942 A1 | 8/2002 | Stanford et al. |
| 2002/0120286 A1 | 8/2002 | Dobrava et al. |
| 2002/0120287 A1 | 8/2002 | Huter |
| 2002/0121472 A1 | 9/2002 | Garner et al. |
| 2002/0123720 A1 | 9/2002 | Kusleika et al. |
| 2002/0123755 A1 | 9/2002 | Lowe et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133092 A1 | 9/2002 | Oslund et al. |
| 2002/0138094 A1 | 9/2002 | Borillo et al. |
| 2002/0138095 A1 | 9/2002 | Mazzocchi et al. |
| 2002/0143360 A1 | 10/2002 | Douk et al. |
| 2002/0143361 A1 | 10/2002 | Douk et al. |
| 2002/0151927 A1 | 10/2002 | Douk et al. |
| 2002/0156456 A1 | 10/2002 | Fisher |
| 2002/0156457 A1 | 10/2002 | Fisher |
| 2002/0161390 A1 | 10/2002 | Mouw |
| 2002/0161392 A1 | 10/2002 | Dubrul |
| 2002/0161393 A1 | 10/2002 | Demond et al. |
| 2002/0161395 A1 | 10/2002 | Douk et al. |
| 2002/0165576 A1 | 11/2002 | Boyle et al. |

| | | |
|---|---|---|
| 2002/0169414 A1 | 11/2002 | Kletschka |
| 2002/0169458 A1 | 11/2002 | Connors, III |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173817 A1 | 11/2002 | Kletschka et al. |
| 2002/0188313 A1 | 12/2002 | Johnson et al. |
| 2002/0188314 A1 | 12/2002 | Anderson et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2003/0004536 A1 | 1/2003 | Boylan et al. |
| 2003/0004537 A1 | 1/2003 | Boyle et al. |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0009188 A1 | 1/2003 | Linder et al. |
| 2003/0009189 A1 | 1/2003 | Gilson et al. |
| 2003/0015206 A1 | 1/2003 | Roth et al. |
| 2003/0018354 A1 | 1/2003 | Roth et al. |
| 2003/0023265 A1 | 1/2003 | Forber |
| 2003/0028238 A1 | 2/2003 | Burkett et al. |
| 2003/0032941 A1 | 2/2003 | Boyle et al. |
| 2003/0032977 A1 | 2/2003 | Brady et al. |
| 2003/0040772 A1 | 2/2003 | Hyodoh et al. |
| 2003/0042186 A1 | 3/2003 | Boyle et al. |
| 2003/0045898 A1 | 3/2003 | Harrison et al. |
| 2003/0057156 A1 | 3/2003 | Peterson et al. |
| 2003/0060782 A1 | 3/2003 | Bose et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0069596 A1 | 4/2003 | Eskuri |
| 2003/0069597 A1 | 4/2003 | Petersen |
| 2003/0078519 A1 | 4/2003 | Salahieh et al. |
| 2003/0078614 A1 | 4/2003 | Satahieh et al. |
| 2003/0083692 A1 | 5/2003 | Vrba et al. |
| 2003/0083693 A1 | 5/2003 | Daniel et al. |
| 2003/0097095 A1 | 5/2003 | Eamon et al. |
| 2003/0100917 A1 | 5/2003 | Boyle et al. |
| 2003/0100918 A1 | 5/2003 | Duane |
| 2003/0105484 A1 | 6/2003 | Boyle et al. |
| 2003/0109824 A1 | 6/2003 | Anderson et al. |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0125764 A1 | 7/2003 | Eamon et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135162 A1 | 7/2003 | Deyette, Jr. et al. |
| 2003/0135232 A1 | 7/2003 | Douk et al. |
| 2003/0139764 A1 | 7/2003 | Levinson et al. |
| 2003/0144685 A1 | 7/2003 | Boyle et al. |
| 2003/0144689 A1 | 7/2003 | Brady et al. |
| 2003/0150821 A1 | 8/2003 | Bates et al. |
| 2003/0153935 A1 | 8/2003 | Mialhe |
| 2003/0153942 A1 | 8/2003 | Wang et al. |
| 2003/0153943 A1 | 8/2003 | Michael et al. |
| 2003/0158574 A1 | 8/2003 | Esch et al. |
| 2003/0163064 A1 | 8/2003 | Vrba et al. |
| 2003/0171770 A1 | 9/2003 | Kusleika et al. |
| 2003/0171771 A1 | 9/2003 | Anderson et al. |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0176889 A1 | 9/2003 | Boyle et al. |
| 2003/0181942 A1 | 9/2003 | Daniel et al. |
| 2003/0181943 A1 | 9/2003 | Daniel et al. |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0195556 A1 | 10/2003 | Stack et al. |
| 2003/0199819 A1 | 10/2003 | Beck |
| 2003/0199921 A1 | 10/2003 | Palmer et al. |
| 2003/0204168 A1 | 10/2003 | Bosme et al. |
| 2003/0204202 A1 | 10/2003 | Palmer et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0208229 A1 | 11/2003 | Kletschka |
| 2003/0212361 A1 | 11/2003 | Boyle et al. |
| 2003/0212429 A1 | 11/2003 | Keegan et al. |
| 2003/0212431 A1 | 11/2003 | Brady et al. |
| 2003/0212434 A1 | 11/2003 | Thielen |
| 2003/0216774 A1 | 11/2003 | Larson |
| 2003/0220665 A1 | 11/2003 | Eskuri et al. |
| 2003/0225418 A1 | 12/2003 | Eskuri et al. |
| 2003/0225435 A1 | 12/2003 | Huter et al. |
| 2003/0229295 A1 | 12/2003 | Houde et al. |
| 2003/0229374 A1 | 12/2003 | Brady et al. |
| 2003/0233117 A1 | 12/2003 | Adams et al. |
| 2003/0236545 A1 | 12/2003 | Gilson |
| 2004/0002730 A1 | 1/2004 | Denison et al. |
| 2004/0006361 A1 | 1/2004 | Boyle et al. |
| 2004/0006364 A1 | 1/2004 | Ladd |
| 2004/0006365 A1 | 1/2004 | Brady et al. |
| 2004/0006366 A1 | 1/2004 | Huter et al. |
| 2004/0006367 A1 | 1/2004 | Johnson et al. |
| 2004/0006368 A1 | 1/2004 | Mazzocchi et al. |
| 2004/0015184 A1 | 1/2004 | Boyle et al. |
| 2004/0019363 A1 | 1/2004 | Hanson et al. |
| 2004/0034385 A1 | 2/2004 | Gilson et al. |
| 2004/0039411 A1 | 2/2004 | Gilson et al. |
| 2004/0044359 A1 | 3/2004 | Renati et al. |
| 2004/0044360 A1 | 3/2004 | Lowe |
| 2004/0049226 A1 | 3/2004 | Keegan et al. |
| 2004/0059372 A1 | 3/2004 | Tsugita |
| 2004/0059373 A1 | 3/2004 | Shapiro et al. |
| 2004/0082967 A1 | 4/2004 | Broome et al. |
| 2004/0082968 A1 | 4/2004 | Krolik et al. |
| 2004/0088000 A1 | 5/2004 | Muller |
| 2004/0088002 A1 | 5/2004 | Boyle et al. |
| 2004/0093009 A1 | 5/2004 | Denison et al. |
| 2004/0093010 A1 | 5/2004 | Gesswein et al. |
| 2004/0093011 A1 | 5/2004 | Vrba |
| 2004/0093012 A1 | 5/2004 | Cully et al. |
| 2004/0093013 A1 | 5/2004 | Brady et al. |
| 2004/0098022 A1 | 5/2004 | Barone |
| 2004/0098026 A1 | 5/2004 | Joergensen et al. |
| 2004/0098032 A1 | 5/2004 | Papp et al. |
| 2004/0098033 A1 | 5/2004 | Leeflang et al. |
| 2004/0102807 A1 | 5/2004 | Kusleika et al. |
| 2004/0106944 A1 | 6/2004 | Daniel et al. |
| 2004/0111111 A1 | 6/2004 | Lin |
| 2004/0116960 A1 | 6/2004 | Demond et al. |
| 2004/0122466 A1 | 6/2004 | Bales |
| 2004/0127933 A1 | 7/2004 | Demond et al. |
| 2004/0127934 A1 | 7/2004 | Gilson et al. |
| 2004/0127936 A1 | 7/2004 | Salaheih et al. |
| 2004/0138693 A1 | 7/2004 | Eskuri et al. |
| 2004/0138694 A1 | 7/2004 | Tran et al. |
| 2004/0138696 A1 | 7/2004 | Drasler et al. |
| 2004/0147955 A1 | 7/2004 | Beulke et al. |
| 2004/0153118 A1 | 8/2004 | Clubb et al. |
| 2004/0153119 A1 | 8/2004 | Kusleika et al. |
| 2004/0158275 A1 | 8/2004 | Crank et al. |
| 2004/0158277 A1 | 8/2004 | Lowe et al. |
| 2004/0158278 A1 | 8/2004 | Becker et al. |
| 2004/0158279 A1 | 8/2004 | Petersen |
| 2004/0158280 A1 | 8/2004 | Morris et al. |
| 2004/0158281 A1 | 8/2004 | Boylan et al. |
| 2004/0167564 A1 | 8/2004 | Fedie |
| 2004/0167565 A1 | 8/2004 | Beulke et al. |
| 2004/0167566 A1 | 8/2004 | Beulke et al. |

| | | |
|---|---|---|
| 2004/0167567 A1 | 8/2004 | Cano et al. |
| 2004/0167568 A1 | 8/2004 | Boyle et al. |
| 2004/0172055 A1 | 9/2004 | Huter et al. |
| 2004/0176794 A1 | 9/2004 | Khosravi |
| 2004/0193208 A1 | 9/2004 | Talpade et al. |
| 2004/0199198 A1 | 10/2004 | Beulke et al. |
| 2004/0199199 A1 | 10/2004 | Krolik et al. |
| 2004/0199203 A1 | 10/2004 | Oslund et al. |
| 2004/0204737 A1 | 10/2004 | Boismier et al. |
| 2004/0210250 A1 | 10/2004 | Eskuri |
| 2004/0220608 A1 | 11/2004 | D'Aquanni et al. |
| 2004/0220609 A1 | 11/2004 | Douk et al. |
| 2004/0220611 A1 | 11/2004 | Ogle |
| 2004/0225322 A1 | 11/2004 | Garrison et al. |
| 2004/0236368 A1 | 11/2004 | McGuckin, Jr. et al. |
| 2004/0236369 A1 | 11/2004 | Dubrul |
| 2004/0249409 A1 | 12/2004 | Krolik et al. |
| 2004/0254601 A1 | 12/2004 | Eskuri |
| 2004/0254602 A1 | 12/2004 | Lehe et al. |
| 2004/0260308 A1 | 12/2004 | Gilson et al. |
| 2004/0260333 A1 | 12/2004 | Dubrul et al. |
| 2004/0267301 A1 | 12/2004 | Boylan et al. |
| 2004/0267302 A1 | 12/2004 | Gilson et al. |
| 2005/0004594 A1 | 1/2005 | Nool et al. |
| 2005/0004595 A1 | 1/2005 | Boyle et al. |
| 2005/0004597 A1 | 1/2005 | McGuckin, Jr. et al. |
| 2005/0010245 A1 | 1/2005 | Wasicek |
| 2005/0010246 A1 | 1/2005 | Streeter et al. |
| 2005/0010247 A1 | 1/2005 | Kusleika et al. |
| 2005/0021075 A1 | 1/2005 | Bonnette et al. |
| 2005/0021076 A1 | 1/2005 | Mazzocchi et al. |
| 2005/0055048 A1 | 3/2005 | Dieck et al. |
| 2005/0070953 A1 | 3/2005 | Riley |
| 2005/0075663 A1 | 4/2005 | Boyle et al. |
| 2005/0080446 A1 | 4/2005 | Gilson et al. |
| 2005/0085842 A1 | 4/2005 | Eversull et al. |
| 2005/0090845 A1 | 4/2005 | Boyd |
| 2005/0090857 A1 | 4/2005 | Kusleika et al. |
| 2005/0090858 A1 | 4/2005 | Pavlovic |
| 2005/0096691 A1 | 5/2005 | Groothuis et al. |
| 2005/0096692 A1 | 5/2005 | Linder et al. |
| 2005/0101986 A1 | 5/2005 | Daniel et al. |
| 2005/0101987 A1 | 5/2005 | Salahich |
| 2005/0101988 A1 | 5/2005 | Stanford et al. |
| 2005/0101989 A1 | 5/2005 | Cully et al. |
| 2005/0113865 A1 | 5/2005 | Daniel et al. |
| 2005/0119688 A1 | 6/2005 | Bergheim |
| 2005/0119689 A1 | 6/2005 | Mazzocchi et al. |
| 2005/0119690 A1 | 6/2005 | Mazzocchi et al. |
| 2005/0119691 A1 | 6/2005 | Daniel et al. |
| 2005/0124931 A1 | 6/2005 | Fulton et al. |
| 2005/0125023 A1 | 6/2005 | Bates et al. |
| 2005/0131450 A1 | 6/2005 | Nicholson et al. |
| 2005/0131453 A1 | 6/2005 | Parodi |
| 2005/0149110 A1 | 7/2005 | Wholey et al. |
| 2005/0149112 A1 | 7/2005 | Barbut |
| 2005/0149113 A1 | 7/2005 | Douk et al. |
| 2005/0159772 A1 | 7/2005 | Lowe et al. |
| 2005/0159773 A1 | 7/2005 | Broome et al. |
| 2005/0159774 A1 | 7/2005 | Belef |
| 2005/0171573 A1 | 8/2005 | Salahieh et al. |
| 2005/0177187 A1 | 8/2005 | Gray et al. |
| 2005/0182440 A1 | 8/2005 | Bates et al. |
| 2005/0182441 A1 | 8/2005 | Denison et al. |
| 2005/0192623 A1 | 9/2005 | Mazzocchi et al. |
| 2005/0192624 A1 | 9/2005 | Mazzocchi et al. |
| 2005/0203567 A1 | 9/2005 | Linder et al. |
| 2005/0203568 A1 | 9/2005 | Burg et al. |
| 2005/0203569 A1 | 9/2005 | Kusleika et al. |
| 2005/0203570 A1 | 9/2005 | Mazzocchi et al. |
| 2005/0203571 A1 | 9/2005 | Mazzocchi et al. |
| 2005/0209634 A1 | 9/2005 | Brady et al. |
| 2005/0209635 A1 | 9/2005 | Gilson et al. |
| 2005/0216051 A1 | 9/2005 | Mazzocchi et al. |
| 2005/0216052 A1 | 9/2005 | Mazzocchi et al. |
| 2005/0216053 A1 | 9/2005 | Douk et al. |
| 2005/0222583 A1 | 10/2005 | Cano et al. |
| 2005/0222604 A1 | 10/2005 | Schaeffer et al. |
| 2005/0222607 A1 | 10/2005 | Palmer et al. |
| 2005/0228437 A1 | 10/2005 | Gilson et al. |
| 2005/0228438 A1 | 10/2005 | Sachar et al. |
| 2005/0228439 A1 | 10/2005 | Andrews et al. |
| 2005/0234502 A1 | 10/2005 | Gilson et al. |
| 2005/0240215 A1 | 10/2005 | Ellis |
| 2005/0245866 A1 | 11/2005 | Azizi |
| 2005/0267517 A1 | 12/2005 | Ungs |
| 2005/0283184 A1 | 12/2005 | Gilson et al. |
| 2005/0283185 A1 | 12/2005 | Linder et al. |
| 2005/0283186 A1 | 12/2005 | Berrada et al. |
| 2005/0288705 A1 | 12/2005 | Gilson et al. |
| 2006/0004403 A1 | 1/2006 | Gilson et al. |
| 2006/0004405 A1 | 1/2006 | Salaheih et al. |
| 2006/0015138 A1 | 1/2006 | Gertner et al. |
| 2006/0015139 A1 | 1/2006 | Tsugita et al. |
| 2006/0015141 A1 | 1/2006 | Linder et al. |
| 2006/0020285 A1 | 1/2006 | Niermann |
| 2006/0020286 A1 | 1/2006 | Niermann |
| 2006/0025803 A1 | 2/2006 | Mitelberg et al. |
| 2006/0025804 A1 | 2/2006 | Krolik et al. |
| 2006/0025805 A1 | 2/2006 | DoBrava et al. |
| 2006/0030876 A1 | 2/2006 | Peacock, III et al. |
| 2006/0030877 A1 | 2/2006 | Martinez et al. |
| 2006/0030878 A1 | 2/2006 | Anderson et al. |
| 2006/0052817 A1 | 3/2006 | Russo et al. |
| 2006/0074446 A1 | 4/2006 | Gilson et al. |
| 2006/0095069 A1 | 5/2006 | Shah et al. |
| 2006/0100659 A1 | 5/2006 | Dinh et al. |
| 2006/0100662 A1 | 5/2006 | Daniel et al. |
| 2006/0100663 A1 | 5/2006 | Palmer et al. |
| 2006/0116715 A1 | 6/2006 | Khosravi et al. |
| 2006/0122643 A1 | 6/2006 | Wasicek |
| 2006/0122644 A1 | 6/2006 | Brady et al. |
| 2006/0122645 A1 | 6/2006 | Brady et al. |
| 2006/0129181 A1 | 6/2006 | Callol et al. |
| 2006/0129182 A1 | 6/2006 | Gilson et al. |
| 2006/0129183 A1 | 6/2006 | Boyle et al. |
| 2006/0149312 A1 | 7/2006 | Arguello et al. |
| 2006/0149313 A1 | 7/2006 | Arguello et al. |
| 2006/0149314 A1 | 7/2006 | Borillo et al. |
| 2006/0155322 A1 | 7/2006 | Sater et al. |
| 2006/0161198 A1 | 7/2006 | Sakai et al. |
| 2006/0167491 A1 | 7/2006 | Wholey et al. |
| 2006/0184194 A1 | 8/2006 | Pal et al. |
| 2006/0190025 A1 | 8/2006 | Lehe et al. |
| 2006/0195137 A1 | 8/2006 | Sepetka et al. |
| 2006/0195138 A1 | 8/2006 | Goll et al. |
| 2006/0200047 A1 | 9/2006 | Galdonik et al. |
| 2006/0200191 A1 | 9/2006 | Zadno-Azizi |
| 2006/0206139 A1 | 9/2006 | Tekulve |

FOREIGN PATENT DOCUMENTS

| | | |
|---|---|---|
| EP | 0472334 A1 | 2/1992 |
| EP | 0533511 A1 | 3/1993 |
| EP | 1 127 556 A2 | 8/2001 |
| EP | 1 127 556 A3 | 8/2001 |
| FR | 2580504 A1 | 10/1986 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |
| WO | WO98/33443 | 8/1998 |
| WO | WO99/16382 | 4/1999 |
| WO | WO99/22673 | 5/1999 |
| WO | WO99/23976 | 5/1999 |
| WO | WO99/44510 | 9/1999 |
| WO | WO00/67667 | 11/2000 |
| WO | WO01/10346 | 2/2001 |
| WO | WO01/12082 | 2/2001 |
| WO | WO01/45592 | 6/2001 |
| WO | WO01/87183 | 11/2001 |
| WO | WO 02/28292 | 4/2002 |
| WO | WO2004/021928 | 3/2004 |

* cited by examiner

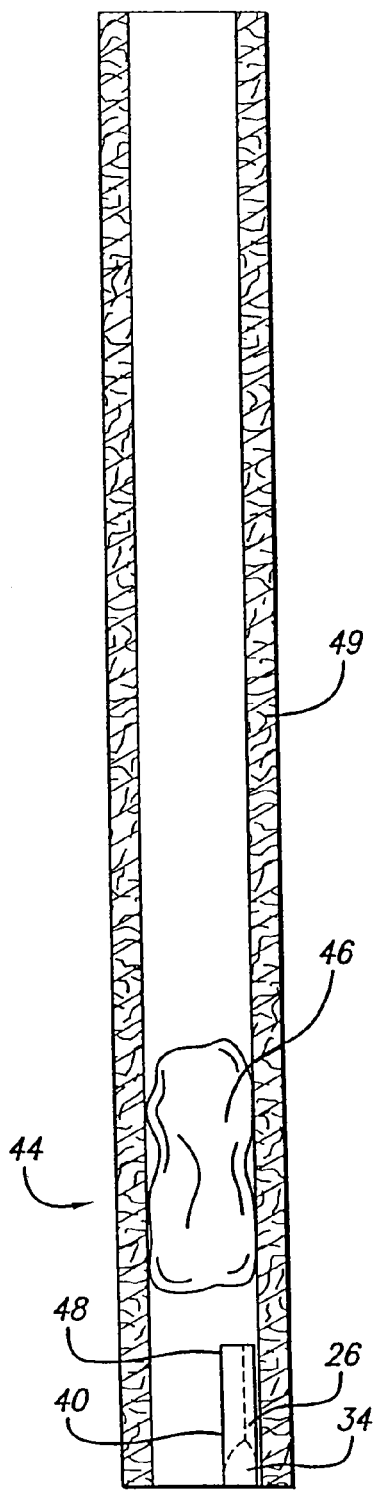
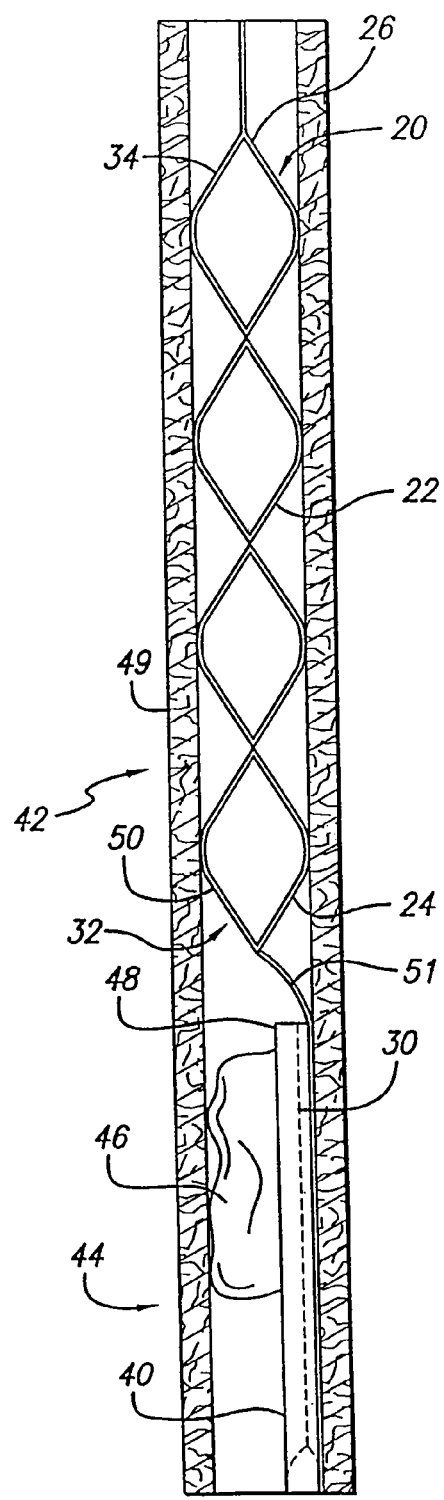

SNARE

CROSS-REFERENCE TO RELATED APPLICATIONS

This is a continuation of U.S. Ser. No. 11/125,578, filed on May 10, 2005 now abandoned; which is a continuation of U.S. Ser. No. 10/457,491, filed on Jun. 9, 2003, U.S. Pat. No. 6,913,612, issued on Jul. 5, 2005; which is a divisional of U.S. Ser. No. 10/123,896, filed on Apr. 15, 2002, U.S. Pat. No. 6,592,607, issued on Jul. 15, 2003; which is a continuation of U.S. Ser. No. 09/469,431, filed on Dec. 23, 1999, U.S. Pat. No. 6,402,771, which issued on Jun. 11, 2002, the contents of which are hereby incorporated by reference.

BACKGROUND OF THE INVENTION

The present invention relates generally to intravascular snare devices and systems and more particularly, devices which can be used to capture embolic material or thrombi found in blood vessels.

The intravascular snare device and system of the present invention is particularly useful when performing balloon angioplasty, stenting procedures, laser angioplasty or atherectomy in critical vessels where the release of embolic debris into the bloodstream can occlude the flow of oxygenated blood to the brain or other vital organs, which can cause devastating consequences to the patient. The snare device is also suited for the removal of clots adhering to vessel walls. While the snare device and system of the present invention is particularly useful in the cerebral vasculature and neurovasculature, the invention can be used in conjunction with any vascular interventional procedure in which there is an embolic risk.

A variety of non-surgical interventional procedures have been developed over the years for opening stenosed or occluded blood vessels in a patient caused by the build up of plaque or other substances on the wall of the blood vessel. Such procedures usually involve the remote introduction of the interventional device into the lumen of the artery, usually through a catheter. In typical carotid PTA procedures, a guiding catheter or sheath is percutaneously introduced into the cardiovascular system of a patient through the femoral artery and advanced, for example, through the vasculature until the distal end of the guiding catheter is in the common carotid artery. A guidewire and a dilatation catheter having a balloon on the distal end are introduced through the guiding catheter with the guidewire sliding within the dilatation catheter. The guidewire is first advanced out of the guiding catheter into the patient's carotid vasculature and is directed across the arterial lesion. The dilatation catheter is subsequently advanced over the previously advanced guidewire until the dilatation balloon is properly positioned across the arterial lesion. Once in position across the lesion, the expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed blood vessel in which cutting blades are rotated to shave the deposited plaque from the arterial wall. A vacuum catheter is usually used to capture the shaved plaque or thrombus from the blood stream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent is crimped tightly onto the balloon portion of the catheter and transported in its delivery diameter through the patient's vasculature. At the deployment site, the stent is expanded to a larger diameter, often by inflating the balloon portion of the catheter.

Prior art stents typically fall into two general categories of construction. A first type of stent is expandable upon application of a controlled force, as described above, through the inflation of the balloon portion of a dilatation catheter which, upon inflation of the balloon or other expansion means, expands the compressed stent to a larger diameter to be left in place within the artery at the target site. A second type of stent is a self-expanding stent formed from, for example, shape memory metals or super-elastic nickel-titanium (NiTi) alloys, which will automatically expand from a compressed state when the stent is advanced out of the distal end of the delivery catheter into the body lumen. Such stents manufactured from expandable heat sensitive materials allow for phase transformations of the material to occur, resulting in the expansion and contraction of the stent.

The above minimally invasive interventional procedures, when successful, avoid the necessity of major surgical operations. However, there is one common problem which can become associated with all of these types of procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, quite often particles are not fully vaporized and thus enter the bloodstream. Likewise, not all of the emboli created during an atherectomy procedure may be drawn into the vacuum catheter and, as a result, enter the bloodstream as well.

When any of the above-described procedures are performed in the carotid arteries, cerebral vasculature, or neurovasculature, the release of emboli into the circulatory system can be extremely dangerous and sometimes fatal to the patient. Naturally occurring debris can also be highly dangerous to a patient. That is, debris which travels through the blood vessel as a natural result of bodily functions and not as a result of an intervention procedure. Debris that is carried by the bloodstream to distal vessels of the brain can cause these cerebral vessels to occlude, resulting in a stroke, and in some cases, death. Therefore, although cerebral percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments that naturally occur or that enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

In addition, the retrieval of fragmented clot may be incomplete, also resulting in emboli and distal occlusions, and further, access through tortuous lumens may prove difficult. Laser-based disruption devices employ the photo-acoustic effect to fragment clot. Local disruption may open up a proximal occlusion but also may cause significant distal emboli.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could otherwise cause problems to the patient's vasculature. Other techniques which have had some limited success include the placement of a filter or trap downstream from the treatment site to capture embolic debris before it reaches the smaller blood vessels downstream. However, there have been problems associated with conventional filtering systems as well. In particular, certain previously developed filtering devices do not optimize the area for embolic collection. That is, conventional filtering devices may not present a collection device that spans the entity of the vessel or it may include supporting structure that itself impedes emboli collection. Certain other devices do not embody sufficient angular resistance to collapse.

Moreover, thrombectomy and foreign matter removal devices have been disclosed in the art. However, in addition suffering from the same disadvantages as certain conventional filter devices, such devices have been found to have structures which are either highly complex or lacking in sufficient or effective expansion and retraction capabilities. Disadvantages associated with the devices having highly complex structure include difficulty in manufacturability as well as use in conjunction with microcatheters. Other less complex devices can pull through clots due to in part to the lack of experience in using the same or otherwise lack an expanded profile that is adequate in capturing clots or foreign bodies.

Furthermore, in current interventional radiology practice, the need arises to remove a variety of objects from intraluminal spaces. Among these are embolic coils, guidewire tips, distal catheter segments, thrombus and other vascular emboli, few of which can be readily removed with current devices. Thrombi-embolic materials can be friable, amorphous, and/or lubricious in nature contributing to this difficulty. Most current therapies rely on grasping, fragmenting, or dissolving the blood-based obstructions. Among the grasping devices are the loop snares and the wire basket snares. These devices may have limited effectiveness, due in part to the lack of encapsulation. Objects are difficult to grasp within these devices, and friable objects, e.g. blood-based blockages, tend to fragment when grasped or pulled, introducing multiple emboli.

Lytic drugs are also used to dissolve blood-based obstructions. These typically have the disadvantages of lengthy treatment/infusion times to remove the obstruction (>3 hrs.), production of emboli, and the potential for systemic iatrogenic bleeding as a side effect of the drug usage. Also, these drugs are not typically effective in removing obstructions that are not blood-based.

What has been needed is a reliable intravascular snare device and system for use when treating blood vessels. The snare devices should be capable of capturing any naturally occurring embolic debris or that which may be released into the bloodstream during an interventional treatment, while minimizing the area occupied by structure supporting the device, and safely containing the debris until the snare device is removed from the patient's vasculature. The devices should embody an expanded profile that presents a consistent radial opening that completely occupies the vessel at the repair site as well as structure for effectively resisting collapse. Moreover, such devices should be relatively easy to deploy and remove from the patient's vasculature and also should be capable of being used in narrow and very distal vasculature such as the cerebral vasculature. The following invention addresses these needs.

SUMMARY OF THE INVENTION

Briefly and in general terms, the present invention is directed towards snares for removing undesired material or objects and restoring patency of blood vessels. The snare is a linked or monolithic framework of thin struts that is radially expansible. The snare of the present invention embodies a structure that provides a consistent radial opening as well as improved radial and angular resistance to collapse. That is, as the device is pulled such as through a vessel, the entrance thereto will not fall back or tip over. Moreover, the snare device maintains clearance in its interior space along its length allowing the material or objects to enter and be captured.

In one aspect of the invention, the snare is manufactured from a tubular element to form struts (members run both generally longitudinally and generally circumferentially) with very small widths and thicknesses and rings (circumferential members) with very small widths and thicknesses but large expansion ratios. The body of the snare device is defined by a plurality of openings bounded by generally longitudinally and generally circumferentially extending members. A proximally extending member is attached to an elongate push member and the assembly is contemplated to be used in conjunction with a generally tubular delivery catheter.

Overall, the intent of the invention is to provide a structure that has the capacity to engage and retain naturally occurring or foreign bodies while having a minimal profile that can traverse easily and repeatably through a standard microcatheter across tortuous anatomy. The device embodies superior flexibility to be deployed and retrieved consistently across difficult anatomy while being able to retain captured material. The inner diameter of the device is heat-set to a pre-determined size. It is envisioned that there be a family of devices that have varying strut lengths, thicknesses, flexibility, and diameters as deemed appropriate for the specific type of vascular or non-vascular setting for which the device is to be used.

In a presently preferred embodiment, the snare device is self-expanding and includes a midsection that forms a generally tubular profile. The proximally extending member projects from a sidewall defining the generally tubular portion to thereby provide a substantially unobstructed radial opening at the proximal end of the snare. A terminal (i.e., distal) end of the snare device can be closed so as to form a pocket for receiving emboli or thrombotic debris. In the event it is desirable to employ a snare device manufactured from a tube embodying both proximal and distal open ends, a woven basket can be attached to the distal end of the device.

The cut tube snare device can assume a number of forms. In one presently contemplated aspect, the snare device of the present invention embodies first and second end portions, a pair of longitudinally spaced rings and a midsection defined by helically extending members. In another aspect, the intravascular snare device has a midsection defined by generally parallel longitudinally extending members. In other aspects, the snare device includes a single convoluted ring or alternatively a body defined by a truncated stirrup-like structure. In yet another embodiment, the snare device has a midsection including almond-shaped apertures as viewed perpendicular to the axis of the snare.

Moreover, the present invention embodies a tip for an endovascular device including an atraumatic soft coil for preventing damage to tissue and facilitates advanceability. The tip further includes multiple layers of coiled material to enhance these objectives as well as to provide stiffness variations.

These and other objects and advantages of the invention will become apparent from the following more detailed description, when taken in conjunction with the accompanying drawings of illustrative embodiments.

BRIEF DESCRIPTION OF THE DRAWINGS

FIG. 1 is a side view, partially in cross-section, of a vessel occluded by debris and a superior portion of a delivery catheter and intravascular snare assembly of the present invention positioned proximate the debris;

FIG. 2 is a side view, partially in cross-section, of the intravascular snare of FIG. 1 deployed within the vessel;

DETAILED DESCRIPTION OF THE PREFERRED EMBODIMENTS

Figure 3:
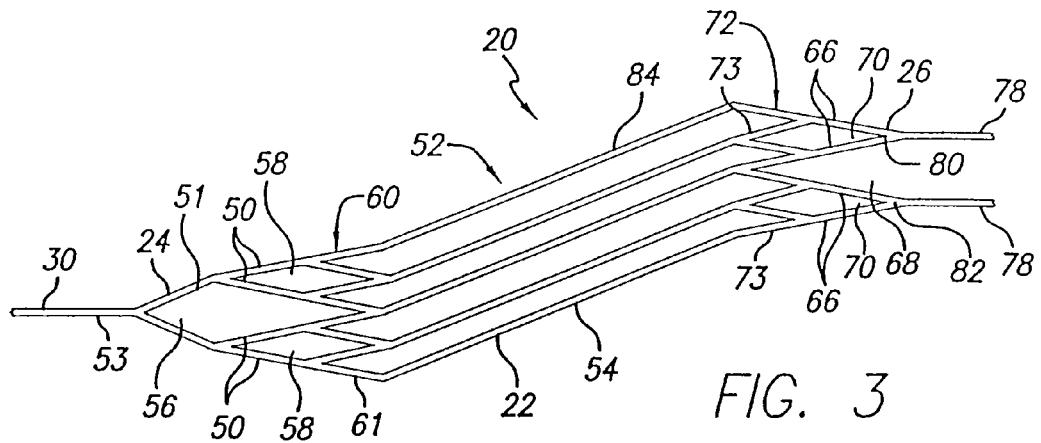
FIG. 3 is a plan view depicting an unrolled pattern of an intravascular snare of the present invention.

Referring now to the drawings, and in particular FIGS. 1 and 2, there is shown the snare device of the present invention. The snare device 20 is adapted to provide more consistent and improved radial opening as well as enhanced angular resistance to collapse. Moreover, the snare device 20 of the present invention is configured to facilitate the maintenance of clearance in its interior space along its length allowing the material or objects to enter and be captured. Furthermore, since it is contemplated that the snare device 20 be manufactured from a tubular member to form elements with very small widths and thicknesses, the device is thus more easily packed to a relatively smaller diameter and inherently embodies high longitudinal flexibility.

The snare device 20 (FIG. 2) of the present invention includes a body 22 having a proximal end portion 24 and a distal end portion 26. The proximal end portion 24 is intended to be affixed to a terminal end portion of an elongate member 30 (described in more detail below). In a presently preferred embodiment, the body 22 of the snare device 20 is generally tubular with a proximally directed opening 32 and a generally closed terminal end 34 to thereby form a basket for receiving embolus, stones, thrombus and foreign bodies found in vasculature or other body cavities.

The snare device 20 for intravascular uses is contemplated to be used in conjunction with a generally tubular delivery catheter 40, such as a microcatheter. Additionally, it is contemplated that a conventional guide catheter (not shown) be used in combination with the delivery catheter 40 loaded with a snare device 20. The guide catheter is employed to provide a guide within a patient's vasculature through which the delivery catheter 40 is inserted. A proximal end of the guide includes a "Y" adapter fitted with sealing, hemostatic valves. The snare device 20 is intended to be self-expandable, however, it is possible to employ an expandable member such as a balloon catheter (not shown) to radially expand a snare device that is not self-expandable, but rather must be deformed to assume an expanded configuration.

In use, the body 22 of a snare device 20 is placed proximally in a compressed configuration coaxially within an internal bore of the generally tubular delivery catheter 20. The longitudinally extending elongate member 30 which is attached to the proximal end 24 of the body 22, is likewise coaxially received within the delivery catheter 40. Both the body 22 and elongate member 30 are slidable within the delivery catheter 40 and accordingly, the delivery catheter 40 and the snare device 20 can be displaced longitudinally with respect to each other.

A typical procedure will now be described. In order to restore patency in a vessel, the snare device/delivery catheter assembly 42 is introduced into a patient's vasculature using conventional means such as the Seldinger technique. Sometimes, a putdown is made to gain access to the patient's vasculature. Using standard endovascular techniques, the emboli in the vasculature is located. The emboli is crossed with the delivery catheter 40 and an appropriate guidewire (not shown). If the vessel is occluded, contrast is injected distal to the occlusion to map the distal vessels. The tip 26 of the delivery catheter 40 is positioned one device length or slightly more beyond the emboli. The guidewire is removed and the snare device 20 is loaded through a rear hub (not shown) of the delivery catheter 20 with the assistance of a conventional introducer sheath (not shown). The snare device 20 is advanced 30-40 cm and the introducer sheath is then removed.

Next, the snare device 20 is advanced until the tip 26 of the basket is at the distal end of the delivery catheter 40. The snare device 20 is held in place and the catheter 40 retracted to allow the device to expand. Holding the snare device 20 in place, the catheter 40 is pulled back until it is proximal to the emboli 46. The entire system is drawn back holding relative positions between the snare device 20 and the catheter 40, allowing the emboli 40 to enter the snare device 20. This step can be assisted with a "stuttering" technique where the snare device 20 is drawn out a small amount, perhaps 1-2 mm, then the elongate member 30 is advanced back perhaps 2 mm to flare the mouth of the snare device 20, assisting clot entry. Then the system is drawn out another 1 mm. This is repeated until the device 20 has traversed a distance about its own length.

If the emboli is foreign in origin, such as a coil, the basket can be moved back and forth past the coil in an iterative attempt to engage the coil in the struts of the basket. When this has occurred, the catheter 40 can be advanced and pinch the coil, locking it into one of the openings of the basket. If the emboli is not radiopaque, its position can be checked by a contrast injection. Also, the radiopaque tip 26 of snare device 20 can be observed during this process. A pulsing motion indicates restored flow.

The system 42 is then drawn back until the distal end of a proximal device marker coil (described below) is at the tip of the guide. At this point, a large syringe, perhaps 60 cc, is attached to the guide catheter at the "Y" adapter on the hub. The guide catheter is aspirated as the snare device 20 and clot 46 are drawn into the guide. Aspiration is maintained until the snare device 20 is fully into the "Y" adapter of the guide catheter, but the snare device 20 is not yet drawn through the hemostatic valve. The "Y" adapter is detached and removed with the snare device in it, allowing a moment of bleed back through the guide to flush any loose clot. Optionally, then a second "Y" arm is attached to prevent excessive bleed back. The guide is then flushed with saline and the entire procedure repeated as required to remove further emboli.

The manner in which the body portion 22 of the snare device 20 self-expands within vasculature and the resultant expansion profile provides a number of advantages. In particular, the body 22 expands to conform to the repair site 44. That is, the generally tubular profile of the body portion 22 substantially conforms to the walls defining the blood vessel 49. Alternatively, the snare device 20 can be sized such that upon full expansion it has a diameter smaller than the diameter of the vessel if desired. Moreover, the expansion of the body 22 facilitates the maintenance of clearance in its interior space along its length allowing the material or objects to enter and be captured and specifically provides a substantially unobstructed access to the proximally directed opening 32 to the body 22. Significantly, as the body 22 self-expands, members 50, 51 leading to the opening 32 to the body 22 are angled or oriented so as to be adjacent the walls defining the blood vessel 49 and are therefore substantially removed from the flow path to thereby provide an unobstructed opening 32.

In its expanded state, the snare device 20 is particularly well-suited to remove embolic or thrombotic debris 46 from the blood vessel 49. As stated, the snare device 20 can be withdrawn proximally so that the debris 46 can be captured by the body 22 of the snare device 20. Alternatively, a separate pusher mechanism (not shown) can be employed to push the debris 46 within the basket defined by the body portion 22. Once the debris has been captured, the snare device 20 and delivery catheter 40 can be removed from the patient's vasculature or the snare device 20 containing the debris 46 can first be pulled within the guide catheter (not shown) and then the assembly 42 removed from the target repair site 44. Also, just the proximal portion can be cinched down to lock the debris without being fully pulled into the delivery catheter 40.

It is to be understood, however, that thrombus or other blood-based material captured within the snare may be eliminated in a variety of ways. For example, the material may be drawn into the guide catheter with the aide of a vacuum applied to the guide catheter, and removed from the body. Also, these materials may be removed from the occluded vessel and allowed to dissolve under natural or induced lytic processes. Alternately, the blood-based material may be inserted into other vasculature more tolerant of occlusion and released.

Referring now to FIG. 3, there is shown one preferred pattern 52 of the snare device 20 of the present invention. As will be developed further below, it is contemplated that the snare pattern 52 be cut from a tubular member using a laser. As best seen in its flattened or unrolled state, the snare pattern 52 composes a body 22 including proximal and distal end portions 24, 26, a midsection 54 and an elongate member 30 extending proximally from the proximal end portion 24.

Figure 8:
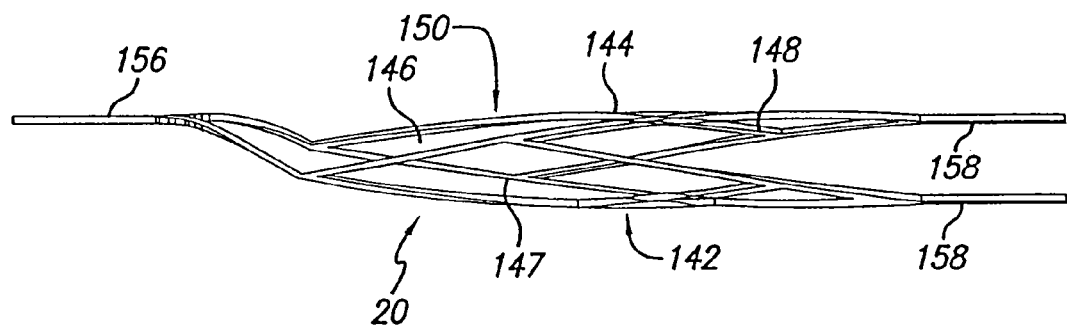
FIG. 8 is a perspective view of the embodiment depicted in FIG. 7.
Figure 9:
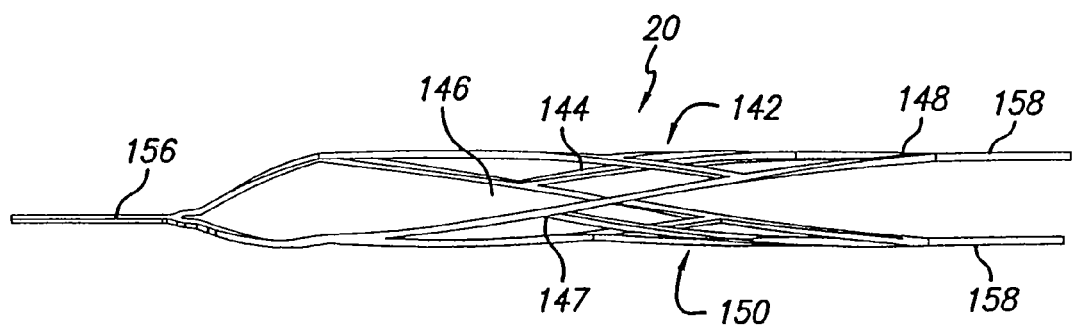
FIG. 9 is another perspective view of the embodiment depicted in FIG. 7.
Figure 10:
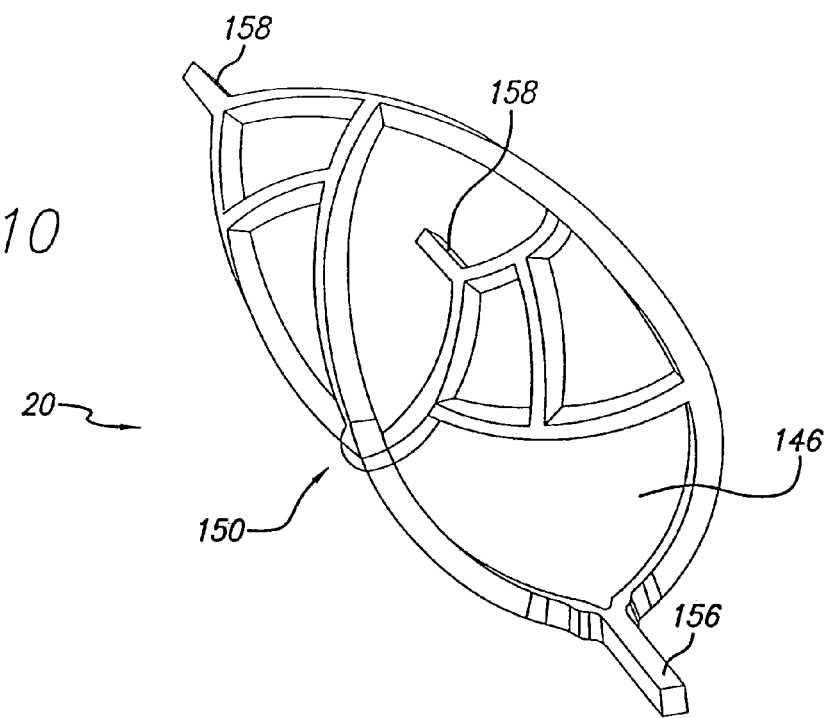
FIG. 10 is an end on view from a proximal end viewpoint of the embodiment depicted in FIG. 7.
Figure 11:
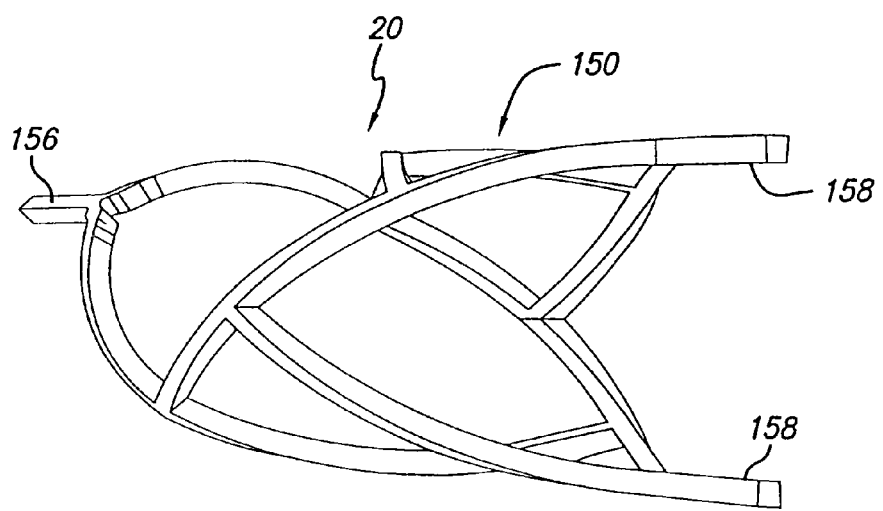
FIG. 11 is an end on view from a distal end viewpoint of the embodiment depicted in FIG. 7.

The proximal end portion 24 includes members or leashes 50 which lead to and aid in defining an opening to the body 22, when in its as cut configuration. The proximal end portion further embodies a pair of connectors 51 extending at an angle from the leashes 50 to thereby accomplish offsetting elongate member 70 from a central axis of the as cut tubular body 22 of snare device 20 as best seen in FIGS. 2 and 8. The connectors 51, in turn, converge to form a proximally directed tab 53 that is connected to the elongate member 30. The leashes 50 and connectors 51 define a centrally located, generally diamond-shaped aperture 56, having a first length, that is substantially sandwiched between two parallelogram-shaped, proximal apertures 58 having a relatively shorter second length. A proximal convoluted ring 60 defined by members 61 arranged in a generally sinusoidal pattern is located distally adjacent the proximal end portion 24. The ring 60 provides for optimal radial opening of the basket-like body 22.

The distal end portion 26 of the snare pattern 52 includes members or leashes 66 which define an open ended, distally directed triangle 68 sandwiched between a pair of two, parallelogram-shaped, distal apertures 70. A distal convoluted ring 72 defined by members 73 arranged in a generally sinusoidal pattern is located proximally adjacent the distal end portion 26. The ring 72 additionally provides for maximal radial opening of the body 27. Distally directed extensions 78 project, in a parallel fashion, from pairs of converging leashes 66.

The midsection 54 of the snare pattern 52 includes a plurality of generally parallel longitudinally extending members 84, each of which are joined at an angle and at one end, respectively, to the proximal ring 60. The other end of these members are joined at an angle to the distal ring 72.

In its as cut form, the terminal ends 80, 82 of the parallelogram-shaped, distal apertures 70 are joined together to form a substantially closed basket. This structure can be joined using soldering or by employing a coil (described hereinbelow) that is wrapped about adjacent structures to form a soft tip. Distally directed extensions 78 may be trimmed to a desired length. The longitudinally extending members 84, while maintaining a parallel relationship, each define a helical pattern to thereby form a generally tubular midsection 54. The helical configuration provides flexibility around bends as well as good foreign body containment. The members 50 form a tapered opening to the generally tubular midsection 54 with the elongate member 30 extending proximally from a sidewall defined by the midsection 54. It is contemplated that the resultant tubular structure, in an unreformed state, includes a longitudinal axis that is parallel to both the elongate member 30 and the distally directed projections 78.

Figure 4:
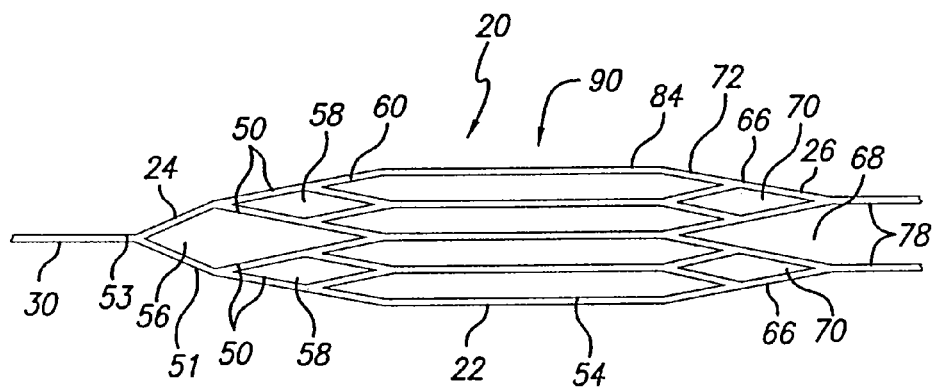
FIG. 4 is a plan view, depicting an unrolled pattern of an alternate embodiment of an intravascular snare of the present invention.

In an alternative embodiment of a snare pattern 90 (FIG. 4), the proximal end and distal end portions 24, 26 also include members 50, 51, 66 which define proximal and distal parallelogram-shaped apertures 58, 70 as well as a diamond-shaped aperture 56 and an open ended triangle 68. This second snare pattern 90 also similarly includes proximal and distal rings 60, 72 as well as distally directed extensions 78, each of which are joined to one of the distal parallelogram-shaped apertures 70. Moreover, the midsection 54 of the pattern 90 includes a plurality of parallel, longitudinally extending members 84 which are joined to the structure defining the proximal and distal end portions 24, 26. This embodiment differs from the first embodiment, however, in that the longitudinally extending members are not helically configured when the pattern 90 is in its as cut form. Rather, while defining a sidewall of a generally tubular midsection 54, each of the longitudinally extending members 84 are parallel to a longitudinal axis of the resultant tubular snare device 20. Being so arranged, the midsection 54 possesses the necessary flexibility to traverse sharp bends in anatomy as well as the capability of being packed into a small profile with minimal bulk.

Further, it is to be recognized that as with the first embodiment, a substantial closed-ended basket is formed by joining via conventional means the terminal ends 78 of the snare pattern 90. Additionally, a tapered opening to a generally tubular midsection 54 is provided by the proximal end portion 24 where the elongate member 30 extends proximally from a sidewall defined by the midsection 54.

Although each of the proximal and distal rings 60, 72 are shown as embodying a four crown design, fewer or more crowns are contemplated. Moreover, there need not be a leash 50, extending from each crown. It is necessary, however, that as with the ring design depicted, the modified pattern also result in rings that provide complete open deployment consistently and reliably. To with, such rings do not fall back. That is, there is no angular deflection when the structure is pulled into a clot or foreign body.

Figure 5:
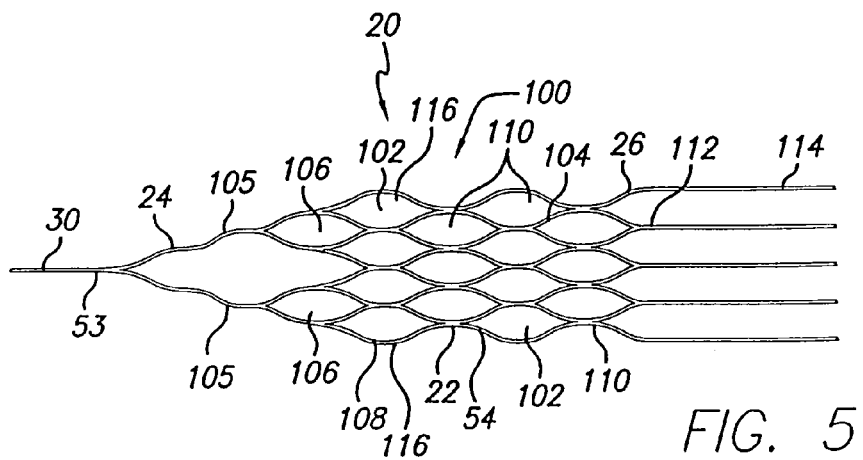
FIG. 5 is a plan view, depicting an unrolled pattern of a further alternate embodiment of an intravascular snare of the present invention.

Turning now to FIG. 5, in yet another embodiment of the snare device 20 of the present invention, a third snare pattern 100 includes a plurality of almond-shaped apertures 102 configured both circumferentially and longitudinally along the snare pattern 100. Each almond-shaped aperture includes curved members 104 shared by adjacent circumferential and longitudinal almond-shaped apertures 102.

The third snare pattern 100 additionally includes an elongate member 30 extending proximally from a pair of converging, undulating members 105 that lead to a first pair of circumferentially spaced, almond-shaped apertures 106 defined by curved members 104. Each of the first pair of circumferentially spaced, almond-shaped apertures 106 are joined and share a portion of a sidewall 104 of two of four almond-shaped apertures defining a first ring 108 of almond-shaped apertures. In a presently preferred embodiment, a series of three additional nested rings 110 of almond-shaped apertures 102, though fewer or more are contemplated, complete a midsection 54 of the third snare pattern 100. Extending from terminal ends 112 of each almond-shaped aperture 102 of the distal most ring 110, is a distally directed extension 114.

In its manufactured form, the third snare pattern 100 has a midsection 54 that defines a generally tubular shape and a closed basket is formed by joining the terminal ends 112 of the most distal ring of apertures 110. Again, the terminal ends may be joined using soldering, laser welding, adhesive, shrink wrap, or by employing a coil configured about adjacent structure.

Figure 7:
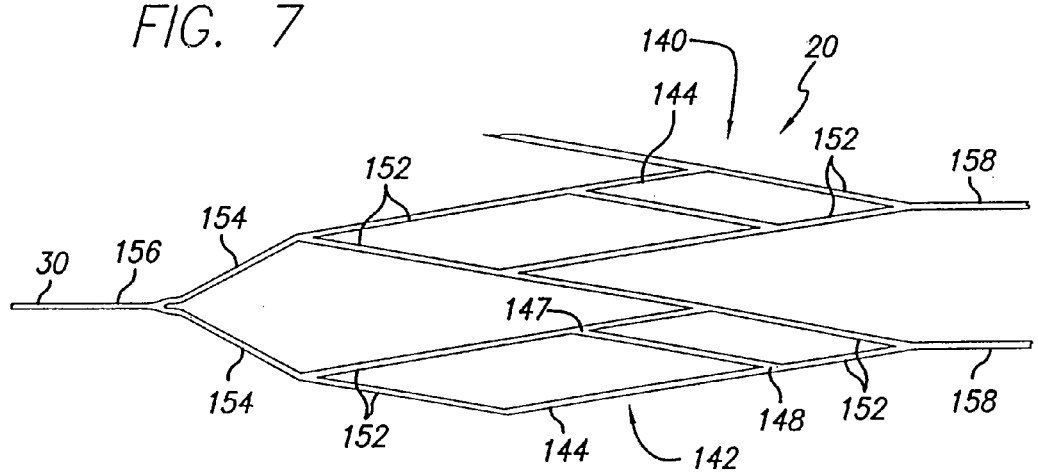
FIG. 7 is a plan view, depicting an unrolled pattern of a fifth embodiment of an intravascular snare of the present invention.

Additionally, the resultant structure includes a tapered opening to the tubular midsection 54 where the elongate member 30 extends proximally from a sidewall defining the tubular midsection 54 and where the elongate member 30 and distally directed members 114 are each parallel to a longitudinal access of the resultant snare device 20. The distally directed members 114 can be trimmed to a desired length. An additional feature of this embodiment (and FIG. 7 described below) is that the curved transitions from tab 53 to converging, undulating members 105 enhances ease of retrieval of the device into a microcatheter.

Figure 6:
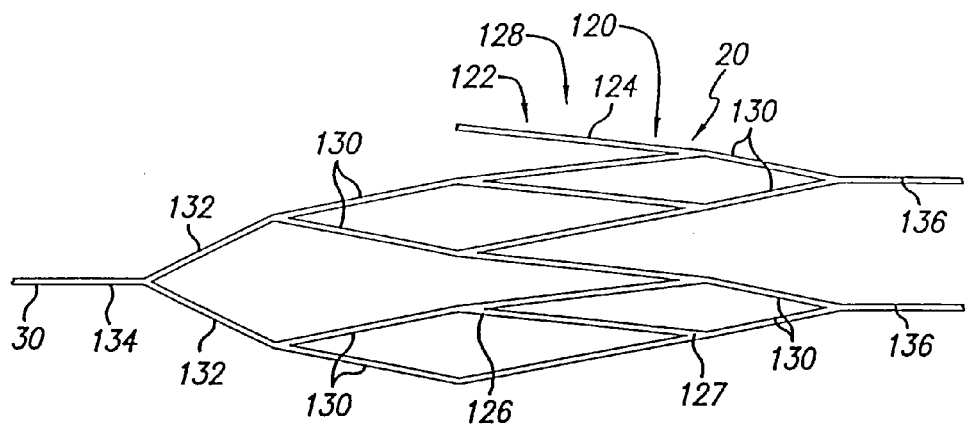
FIG. 6 is a plan view, depicting an unrolled pattern of a fourth embodiment of an intravascular snare of the present invention.

In a fourth embodiment (FIG. 6), the snare device 20 embodies a snare pattern 120 that includes a single conventional ring 122 defined by a continuous set of interconnected members 124. The interconnected members 124 are composed of straight struts that together define a central lumen in the manufactured form. The members 124 converge at ends thereof to form four proximal and distal crowns or vertices 126, 127 on each side of the ring 122. The ring 122 serves as a central body 128 of the snare device 20.

A single member 130 extends from each of the four crowns 126, 127 of the ring in both proximal and distal directions. Proximally, the four members 130 converge into two members 132, which again converge into a single member 134. This single proximal member 134 serves as a tab for attachment to the elongated member 30.

Extending from each of the members 130 projecting from the distal crowns 127 is a single distally directed extension 136. The distally directed extensions 136 can be configured to form an atraumatic tip as described herein below.

In a fifth embodiment (FIG. 7), the snare device 20 has a pattern 140 similar to that of the fourth embodiment. In particular, this pattern also includes a convoluted ring 142 defined of a continuous set of interconnected members 144. The interconnected members 144 are composed of straight sections that together form a central lumen 146 (see FIGS. 8-11) in the manufactured form. The members converge at terminal ends thereof to form four proximal and distal crowns 147, 148 on each side of the ring 142, which serves as a central body 150 of the device 20. In this embodiment, however, alternative crowns 147, 148 at each end of the ring 142 are offset longitudinally from each other. Thus, every other interconnecting member 144 has a different length.

As with the fourth embodiment, a single member 152 extends from each of the four crowns 147, 148 in both proximal and distal directions. Further, the four members 152 connected to the proximal crowns 147 converge into two members 154, each of which again converge to form a proximal tab 156. At the distal end of the device 20, adjacent pairs of the single members 152 converge to a single extension 158. Again, the terminal ends 158 may be joined using soldering, laser welding, adhesive, shrink wrap, or by employing a coil configured about adjacent structure.

Figure 12:
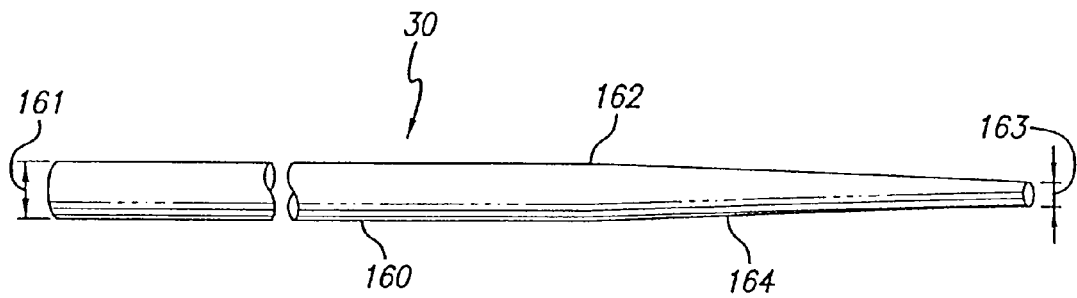
FIG. 12 is a side view, depicting an elongate member of the present invention.

Referring now to FIG. 12, there is shown one preferred embodiment of the elongated member 30 of the present invention. The member 30 embodies a gradual or step-tapered core comprising a proximal section of 304V stainless steel and a distal section of nitinol or an equivalent material for the intended purpose. A proximal portion 160 of the member 30 has a generally constant cross-sectional profile and a first diameter 161. At a transition point 162, the member 30 begins to taper in a gradual and consistent, alternatively in a step-tapered manner, from the first diameter 161 to a second diameter 163 along a distal end portion 164.

Figure 13:
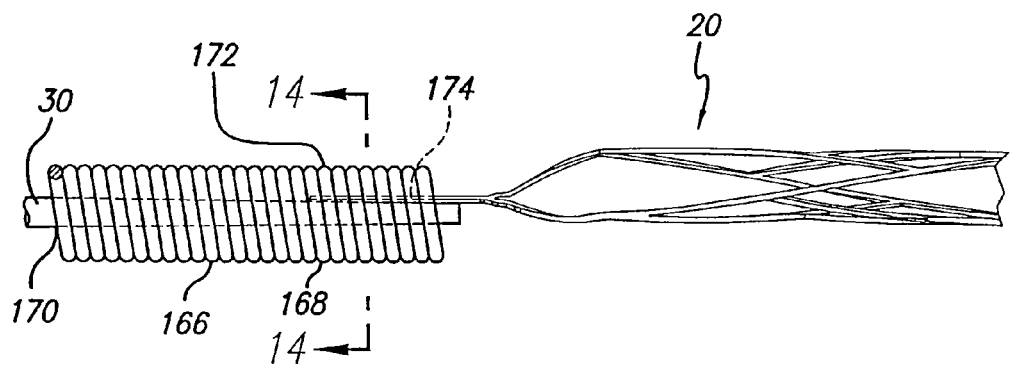
FIG. 13 is a side view, partially in cross-section, depicting a plurality of coils configured about a distal end portion of the elongate members in combination with a snare device of the present invention.
Figure 14:
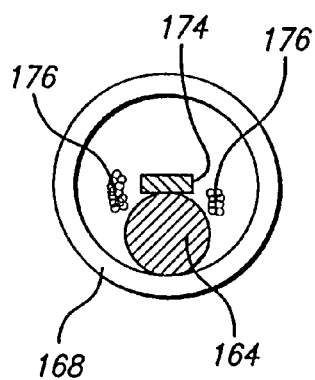
FIG. 14 is a cross-sectional view, taken along lines 14-14 depicting the assembly of FIG. 13.

As shown in FIGS. 13 and 14, a pair of longitudinally adjacent arranged coils 166, 168 are employed to attach a proximal tab 174 of a snare device 20 to the distal end portion 164 of the elongate member 30. The first, proximal coil 166 is contemplated to be composed of 304V stainless steel, the first coil being soldered to the elongate wire 30 near its tapered portion 170. The second coil 168 is contemplated to be comprised of about 90% platinum and 10% iridium alloy. This second coil 168, which serves as a radiopaque marker, is soldered to the elongate member 30 near a distal end portion 172 of the first coil 166. Alternatively, the second coil 168 is soldered to the first coil 166. A proximal tab 174 of the snare device 20 is contained within the second coil 168 and is soldered 176 to the elongate member 30.

Figure 15:
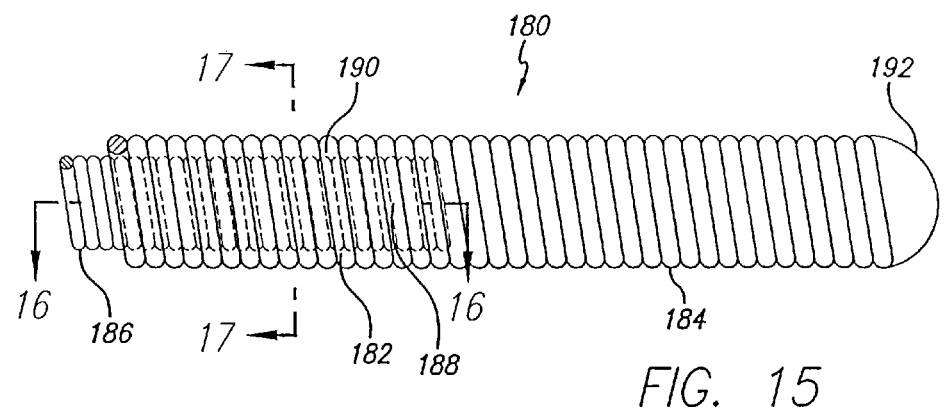
FIG. 15 is a side view, partially in cross-section, depicting a distal end portion of a tip of the snare device of the present invention.
Figure 16:
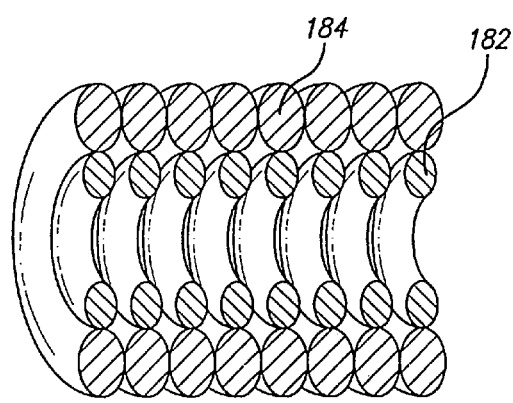
FIG. 16 is a cross-sectional view, taken along lines 16-16 of FIG. 15, depicting a portion of the assembly of FIG. 13.
Figure 17:
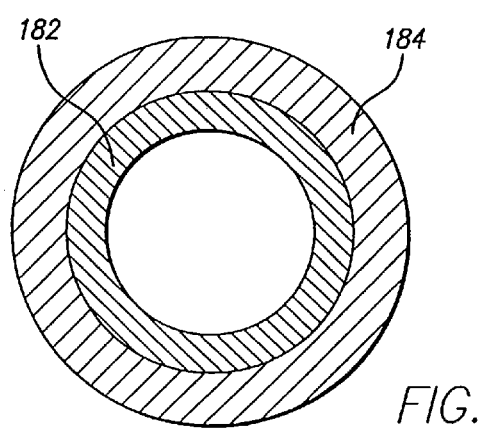
FIG. 17 is a cross-sectional view, taken along lines 17-17 of FIG. 15, depicting the assembly of FIG. 13.

Turning now to FIGS. 15-17, one presently preferred embodiment of a distal tip portion 180 of the snare device 20 of the present invention is described. The distal tip portion 180 is comprised of two partially coaxial coils 182, 184, the combination of which retains the extensions projecting from the body of the snare device 20. The combination also provides a soft atraumatic tip with variable stiffness from softest distally to stiffer proximally.

The inner coil 182 is comprised of nitinol or equivalent material, and begins at a proximal location 186 and extends to a distal location 188. The nitinol inner coil 182 provides kink resistance as well as creates a smooth stiffness transition from the tip of the basket portion of the snare device 20. The outer coil 184 is coaxially configured about a distal portion 190 of the inner coil 182 and is preferably comprised of 90% platinum and 10% iridium alloy or an equivalent combination of materials. As such, the outer coil 184 can operate as a radiopaque marker.

The distal tip portion 180 further includes a rounded terminal end 192 that provides a blunt atraumatic surface. The terminal end 192 embodies a soldered joint which acts in retaining the helical configuration of the outer coil 184.

Figure 18:
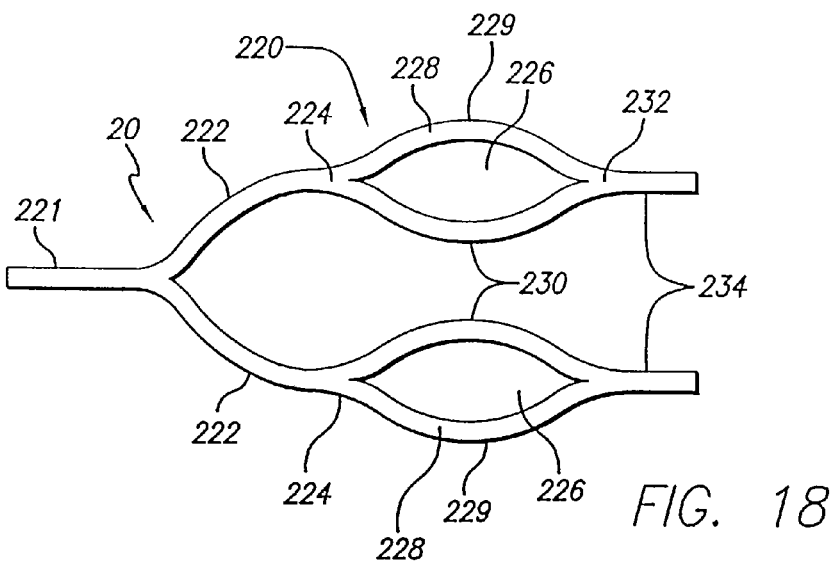
FIG. 18 is a plan view, depicting a portion of an unrolled pattern of yet another embodiment of an intravascular snare of the present invention.
Figure 19:
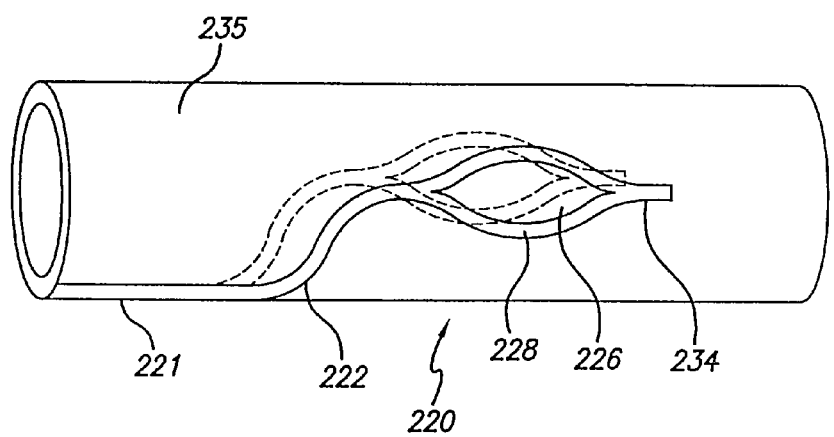
FIG. 19 is a perspective side view, depicting one step of a manufacturing process used to produce the snare device of FIG. 16.
Figure 20:
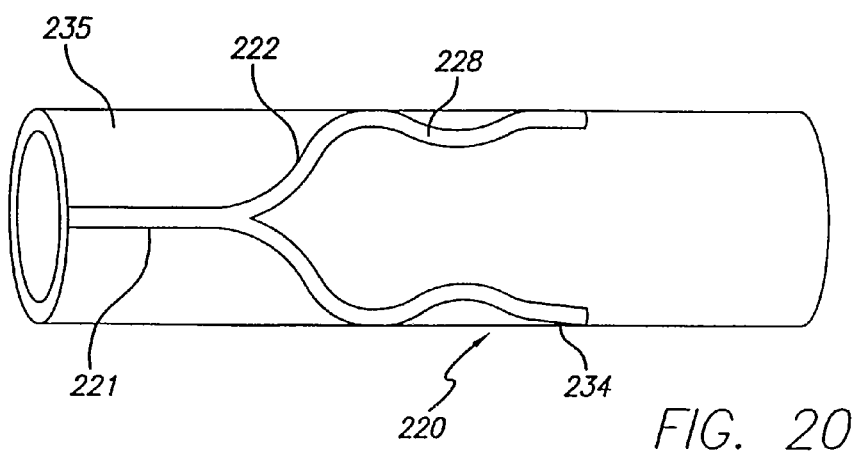
FIG. 20 is a perspective bottom view, depicting one step of a manufacturing process used to produce the snare device of FIG. 16.

With reference to FIGS. 18-20, a brief summary of the process used to manufacture the snare devices 20 of the present invention is provided, with a specific focus on a sixth embodiment of the present invention. As shown in FIG. 18, the sixth embodiment is relatively similar to a truncated third embodiment and defines a general stirrup-shaped pattern 220. This stirrup pattern 220 also includes a proximally directed tab 221 and a pair of diverging members 222 extending from the tab 221. Configured at each terminal end 224 of the diverging members 222 is a single almond-shaped aperture 226 defined by curved members 228. The curved members 228 further include apices 229, 230 defining outer edges of the curved member 228. Moreover, joined to a distal end 232 of each almond-shaped opening 226 is a distally directed extension 234.

It is contemplated that the snare devices 20 of the present invention be cut from a tube 235 (FIGS. 19 and 20) using conventional means such as a laser. In particular, a specific pattern is programmed into the laser device and the laser is activated to cut the desired pattern into the tubular element 235. The excess tubular components are removed, thereby leaving a manufactured structure such as the stirrup snare pattern 220 shown in FIGS. 19 and 20, corresponding to the desired pattern. In a presently preferred embodiment, a super elastic material such as nitinol is a material of choice for the snare device 20. Thereafter, post-processing such as surface treatment, burr removal and deformation of the manufactured structure is performed. Heat treating is also performed for sizing the device.

In particular, post-processing steps include taking an as-cut device and bead blast the device with aluminum oxide blasting media. The device is then inspected under a microscope for residual slag. If slag remains, the device is bead blasted again. Thereafter, the device is heat-treated in a molten salt bath without expanding. The device is subsequently heat-expanded in a molten salt bath mounted on a suitable size mandrel. After heat expansion, surface oxidation is removed in an aqua regia bath. When nitinol is the material of choice, the nitinol is etched with HF solution to desired softness or strut size. The device is then mounted on a guidewire.

In the case of the stirrup pattern 220, the post-processing may include deforming the pattern 220 and then joining together the distal end members 234 as well as adjacent apices 229, 230 for the purpose of achieving a closed basket for receiving debris found in vasculature. Being so configured, the pair of diverging members 222 define an opening to the resultant basket and the elongate member 30 extends from a sidewall defined by the pocket. Alternatively, distal end members 234 can be left apart and a basket attached to them as described below.

Figure 21:
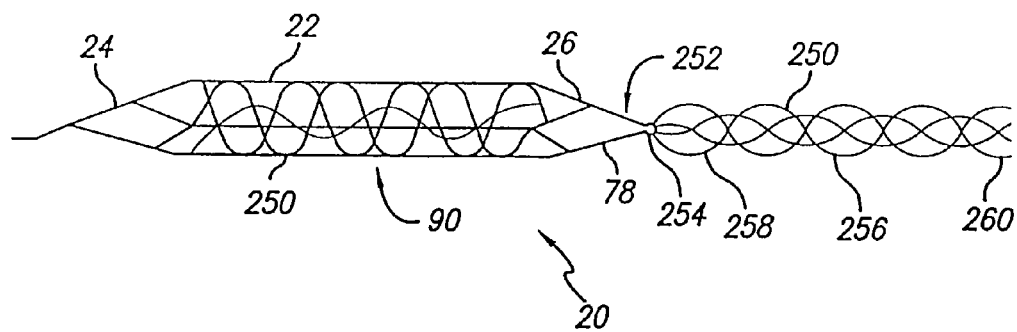
FIG. 21 is a side view, depicting an assembled snare device of FIG. 4 of the present invention including a braided structure for capturing emboli.

It is contemplated that certain circumstances may dictate other forms of a snare device 20. In particular, it is contemplated that a braided structure can be attached to a distal end portion of any of the previously described snare patterns. A braid can also be attached along the length of the body of the snare device. As shown in FIG. 21, one such braided structure 250 can be attached to, for example, a distal end portion 26, as well as the body snare pattern 90. In such a case, rather than terminating with distally directed members 78, the snare device 20 can include terminal apices 252 forming loops 254.

In one presently preferred embodiment, members 256 defining a first end 258 of the braided structure 250 can be attached to the loops 254 of the terminal apices 252 by conventional means. A second end 260 of the braided structure 250 can remain in an open configuration, or alternatively, members 256 defining the second end 260 can be joined to form a closed elongated tube.

The snare/braid assembly provides a number of advantages. In particular, such an assembly embodies additional volume for collecting debris from vasculature. Additionally, the braided structure includes sidewalls characterized by a higher density which can, in certain circumstances, be better suited for capturing relatively smaller debris found in vasculature.

Figure 22:
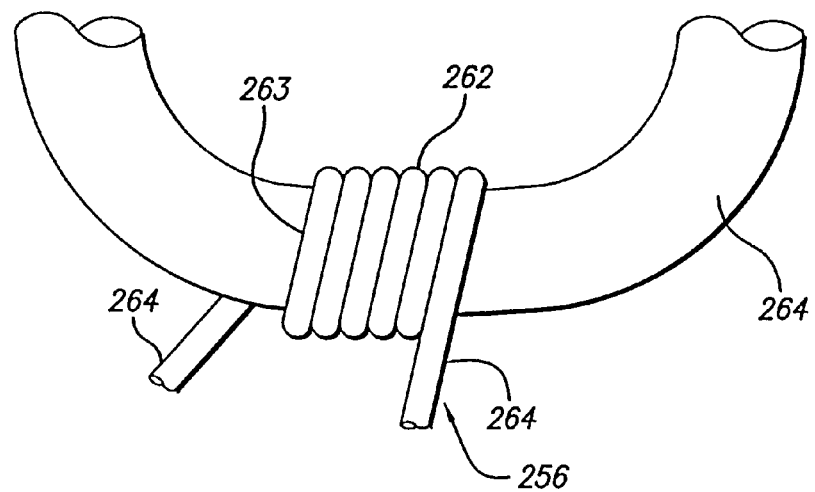
FIG. 22 is a perspective view, depicting one manner of attachment of the braided structure of FIG. 21 to a loop.

Turning to FIG. 22, it is important that the leading edges 262 of the connection between the braided structure 250 and the loops 254 formed in the distal end portions of a snare pattern be as atraumatic as possible. In one presently preferred embodiment, the members 250 defining a first end 258 of the braided structure 250 are configured into a two-legged coil 263 routed such that legs 264 of the coil extend from an outer surface of the loops 254 formed in the distal end portion 26. The coil is heat-set to enhance the connection to the snare pattern. It is also contemplated that single-leg coils (not shown) could additionally be used for attachment in the event forces required to unravel the single-leg coil are greater than the force necessary to deploy and retract the braided structure 250. An atraumatic leading end, however, remains an objective, as well as space considerations (i.e., low profile for packing into microcatheter).

The snare devices of the present invention compared to prior art loop snares each provide improved radial opening since in an expanded state, the elongate member 30 is positioned substantially out of the flow path. Additionally, the device embodies improved resistance to radial loads compared to prior art loop snares. Moreover, since less deformation is required to produce a desired snare pattern, in that, angles between members are provided by laser cutting rather than from local deformations, for example, there is improved stress distribution along the snare devices of the present invention compared to prior art loop snares. Additionally, a greater reduction in radial profile can be achieved without sacrificing performance and in particular, the device can be used in conjunction with microcatheters. As such, the snare devices 20 of the present invention can be passed through narrow and tortuous vasculature. The applications of the present invention are more widespread than that of conventional snare devices because of greater retrieval characteristics while retaining the deliverability characteristics.

The above described invention is principally conceived to be operational for use in engaging for the purpose of displacing and/or removing material either foreign or native to the body, including partial or complete obstructions embolic and/or thrombotic in nature, from intraluminal or extraluminal spaces of the body including but not limited to intravascular and/or intra-arterial regions of the neurovasculature, as well as tubings, stents, or other objects that may or may not be internal to the body. The purpose of the device is to restore functionality of the luminal space or systems dependent on the particular luminal space or as a method of producing any desired effect associated with the removal or displacement of undesirable material.

The intended delivery of the disclosed invention is by means of a commercially available catheter selected to its ability to access the desired location of engagement. The invention may be optimized for specific locations or uses by means of sizing the individual elements in the design and/or the overall dimensions, as well as selection of materials, mesh configuration, number and relative geometry of component members to meet the requirements of the operational space. Optimizations may include tabs protruding from the sides of members to increase coverage of the open areas between members, offsetting vertices of joints to increase packing efficiency, or providing unconnected distal curved path. There may additionally be variations of the dimensions of length, thickness, and width of distal and proximal tabs for joining basket with delivery wire and distal tip to provide smooth stiffness transitions from tip to basket and basket to delivery wire. Such optimizations are means of adjusting operational attributes including: flexibility, applied circumferential force, engagement effectiveness, deliverability and traversal through tortuous vasculature, and volume of material to be engaged.

Alternate or additional materials for the basket portion of the device may include a thermoset, elastomer, thermoplastic constituents such as nylon, or other metal either pure or alloyed, as well as composite materials such as a combination of glass, aramid, or carbon in a binding matrix. A secondary mesh of the same or dissimilar material may be added to the basket. The wire portion of the device can alternatively be made from a single metal or combination of metals for kink resistance and high flexibility. Either or both components may be tapered to give a transition in stiffness that is appropriate for the vessel in which the invention is to be delivered. The distal tip of the device may incorporate concentric coils made of nitinol, stainless steel, or other metal or plastic to provide a soft flexible atraumatic end.

An alternate method of manufacture of the basket portion of the device may be etching, or metal or polymer injection molding. Furthermore, the device may employ any combination of coatings, agents, or features including those of that result from material addition or subtraction to create grooves, bumps, three dimensional patterns, and textures on inner and/or outer surfaces or any combination thereof to promote desired properties such as adherence of materials to be engaged, radiopacity, and low friction between the device and the vessel wall or microcatheter lumen.

In summary, the invention is deliverable to remote regions of the neurovasculature by gaining access through the use of a guidewire and microcatheter in the vasculature and subsequent deployment of the invention through the lumen of the microcatheter. In a vessel in which flow is impeded or obstructed by material and/or objects including those formed by the body such as blood clot, the device is deployed by withdrawing the microcatheter relative to the wire. Engagement occurs as the system composed of the invention and microcatheter is pulled into the material. After the material has been engaged, removal of the material is accomplished by withdrawing the system into a guide catheter lumen through which the microcatheter is passed with or without simultaneously pulling fluid through the guide lumen.

Thus, it will be apparent from the foregoing that, while particular forms of the invention have been illustrated and described, various modifications can be made without the parting from the spirit and scope of the invention. Accordingly, it is not intended that the invention be limited, except as by the appended claims.

What is claimed is:

1. A snare device for use in vasculature, comprising:
  an elongate member having a first end and a second end;
  a distal tip portion located on the second end of the elongate member, the distal tip portion including a first coil and a second coil, the second coil being disposed adjacent to the first coil, the first and second coils being made from different materials; and
  a body configured to engage or capture material found in the vasculature, the body including a proximally extending tab which is attached to the distal tip portion of the elongate member, wherein at least a portion of the second coil is disposed over at least a portion of the proximally extending tab.

2. The device of claim 1, wherein the distal tip portion includes a blunt terminal end formed from a solder joint.

3. The device of claim 1, wherein the first coil is made from nitinol.

4. The device of claim 3, wherein the second coil is made from an alloy made from about 90% platinum and about 10% iridium.

5. The device of claim 1, wherein the distal tip portion includes a weld which connects the proximally extending tab to the distal end of the elongate member.

6. The device of claim 1, further including a weld connecting the first coil to the distal end of the elongate member.

7. The device of claim 6, further including a weld connecting the first coil to the second coil.

8. The device of claim 1, further including a weld connecting the second coil to the distal end of the elongate member.

9. The device of claim 1, further includes a weld which connects the proximally extending tab to the distal end of the elongate member.

10. The device of claim 1, wherein the body includes a distal end having a distal tip made from an inner coil and an outer coil attached thereto, the outer coil being coaxially disposed about at least a portion of the inner coil.

11. The device of claim 10, wherein the inner coil is made from nitinol.

12. The device of claim 11, wherein the outer coil is made from an alloy made from about 90% platinum and about 10% iridium.

13. The device of claim 10, wherein at least a portion of the body extends distally from the distal end of the elongate member.

14. The device of claim 1, wherein the first coil is made from stainless steel.

15. The device of claim 14, wherein the second coil is made from an alloy made from about 90% platinum and about 10% iridium.

16. The device of claim 1, wherein at least a portion of the body extends distally from the distal end of the elongate member.

* * * * *